United States Patent [19]
Schnaar et al.

[11] Patent Number: 5,962,434
[45] Date of Patent: Oct. 5, 1999

[54] COMPOUNDS FOR STIMULATING NERVE GROWTH

[75] Inventors: Ronald L. Schnaar, Columbia; Lynda J. S. Yang, Baltimore, both of Md.; Akira Hasegawa, Gifu, Japan

[73] Assignee: The Johns Hopkins University School of Medicine, Baltimore, Md.

[21] Appl. No.: 08/702,787

[22] Filed: Aug. 23, 1996

Related U.S. Application Data

[60] Provisional application No. 60/002,832, Aug. 25, 1995.

[51] Int. Cl.$^6$ .............................. A61K 31/715; C07H 5/04
[52] U.S. Cl. ............................... 514/54; 514/25; 435/7.1; 536/53; 536/55.1
[58] Field of Search .................. 514/54, 25; 435/7.1; 536/53, 55.1

[56] References Cited

FOREIGN PATENT DOCUMENTS 5-230103  9/1993  Japan .

OTHER PUBLICATIONS

Hirabayashi et al. *The Journal of Biological Chemistry* Jun. 25, 1992, 267(18), 12973–12978.

Munesada et al. *J. Chem. Soc. Perkin Trans. I* 1989, 1491–1496, month not available.

Yang, et al. *Gangliosides are Neuronal Ligands for Myelin–associated Glycoprotein*, Proc. Natl. Acad. Sci., 93:814–818, Jan. 1996.

Wietholter, H., et al., *Influence of Gangliosides on Experimental Allergic Neuritis*, Journal of Neuroimmunology, 38:221–228, 1992.

Nakajima, et al., *Bioactive Gangliosides: Analysis of Functional Structures of the Tetrasialoganglioside $G_{Q1b}$ Which Promotes Neurite Outgrowth*, 876:65–71, 1986.

Matta, et al., *Neuritogenic and Metabolic Effects of Individual Gangliosides and their Interaction with Nerve Growth Factor in Cultures of Neuroblastoma and Pheochromocytoma*, Developmental Brain Research, 27:243–252, 1986, no month available.

*Primary Examiner*—Kathleen K. Fonda
*Attorney, Agent, or Firm*—Fish & Richardson P.C.

[57] ABSTRACT

Compounds which can stimulate neuronal growth by inhibiting the neuronal inhibitory activity of myelin-associated glycoprotein (MAG), and a method of using the compounds for stimulating neuronal growth are provided. The invention further provides a method of identifying compounds which inhibit myelin-associated glycoprotein inhibition of axonal outgrowth of injured nerve cells. The method involves contacting the compound with myelin-associated glycoprotein under conditions which allow myelin-associated glycoprotein and the compound to bind and detecting the binding.

20 Claims, 13 Drawing Sheets

| Compound # | R1 | R2 | R3 | R4 |
|---|---|---|---|---|
| 1 | NHAc | H | benzylidene | |
| 2 | NHAc | Lev | benzylidene | |
| 3 | NHAc | Lev | H | H |

Compound 4

Compound 7

Compound #12

Compound 15

Compound 16

| Compound # | R1 | R2 | R3 | R4 |
|---|---|---|---|---|
| 17 | OSE | H | Bn | H |
| 18 | OSE | H | Ac | Ac |
| 19 | OH,H | OH,H | Ac | Ac |
| 20 | H | OC(=NH)CCl3 | Ac | Ac |

Compound 23

COMPOUNDS FOR STIMULATING NERVE GROWTH

The present invention claims priority under 35 U.S.C. §119(e)(1) from U.S. Provisional Application Ser. No. 60/002,832, filed Aug. 25, 1995.

This invention was made with government support under NIH Grant/Control number HD14010 awarded by the National Institutes of Health. The government nay have certain rights in this invention.

BACKGROUND OF THE INVENTION

1. Field of the Invention

This invention relates to methods of identifying and using compounds for stimulating nerve growth. In particular, this invention relates to complex carbohydrate compounds for stimulating nerve regrowth after injury.

2. Description of the Related Art

Nerve cell function depends upon appropriate contacts between the neuron and other cells in its immediate environment (U. Rutishauser, T. M. Jessell, *Physiol. Rev.* 68:819, 1988). These cells include specialized glial cells, oligodendrocytes in the central nervous system (CNS), and Schwann cells in the peripheral nervous system (PNS), which ensheathe the neuronal axon with myelin, which is an insulating structure of multi-layered membranes (G. Lemke, in *An Introduction to Molecular Neurobiology*, Z. Hall, Ed. [Sinauer, Sunderland, Mass., 1992], p. 281.).

Myelin is required for efficient nerve impulse conduction, but has other profound biological effects. The inability of nerves to regenerate after CNS injury in adults may be due largely to the axon'inability to grow when in contact with CNS myelin (P. Caroni, T. Savio, M. E. Schwab, *Prog. Brain Res.* 78:363, 1988; M. E. Schwab, J. P. Kapfhammer, C. E. Bandtlow, *Annu. Rev. Neurosci.* 16:565, 1993). Central nervous system injuries are particularly devastating because, unlike peripheral nerves, central nerves do not regenerate, so that central nervous system damage is usually permanent.

While CNS nerve cells have the capacity to regenerate after injury, they are inhibited from doing so by molecules normally found in their local environment. One such molecule is on myelin (Mukhopadhyay, G., et al. *Neuron* 13:757–767, 1994; McKerracher, L., et al. *Neuron* 13:805–811, 1994), and is referred to as myelin-associated glycoprotein (MAG). It would be desirable to identify molecular factors which interfere with the ability of MAG to inhibit nerve growth. Knowledge of those factors would form a basis for developing drug therapies to interfere with MAG's inhibitory effects, thus enhancing regeneration of nerves. The present invention provides a method to address these needs, and provides improved methods for treating nerve injury.

SUMMARY OF THE INVENTION

For the first time, compounds have been identified which can stimulate neuronal growth by inhibiting the neuronal inhibitory activity of myelin-associated glycoprotein (MAG). Based on this discovery, it is an object of the invention to provide a compound, and pharmaceutical compositions thereof, which specifically bind with MAG in order to inhibit nerve growth-inhibiting MAG-nerve interactions, thereby inhibiting the MAG-mediated inhibiting mechanism so that nerve cell axons regrow after injury.

It is another object of the present invention to provide a method to identify molecules or compounds which, when bound to MAG, allow MAG to inhibit nerve cell regrowth. Such identified compounds, when exogenously supplied, inhibit MAG inhibition of axonal growth.

A further object of the invention is to provide a method for treating injured nerve cells using the compounds identified by the invention.

The invention provides a method for stimulating neuronal growth comprising contacting nerve cells with a composition comprising a therapeutically effective amount of a complex carbohydrate. The complex carbohydrate has sufficient binding capacity to myelin-associated glycoprotein to induce axonal growth by interrupting the inhibitory effects of myelin-associated glycoprotein. The complex carbohydrate has the terminal sequence:

wherein
  A is N-acetylgalactosamine,
  B is galactose,
  C is glucose, and
  L is H or a hydrophobic group, and
wherein the linkage of NeuAc-Gal is NeuAc α2,3 Gal.

The invention further provides a method of identifying a compound which inhibits myelin-associated glycoprotein inhibition of axonal outgrowth of injured nerve cells. The method involves contacting the compound with myelin-associated glycoprotein under conditions which allow myelin-associated glycoprotein and the compound to bind and detecting the binding.

Further provided is a glycolipid having the structure

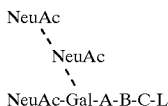

wherein the linkage of NeuAc-Gal is NeuAc α2,3 Gal, and wherein Gal-A-B-C is gangliotetraose, and L is H or a hydrophobic group. The glycolipid has sufficient binding affinity for MAG to enhance axonal growth when brought in contact with nerve cells for a sufficient period of time.

These and many other features and attendant advantages of the present invention will become better understood by reference to the following detailed description of the invention when taken in conjunction with the Examples.

DESCRIPTION OF THE INVENTION

Figure 1A:
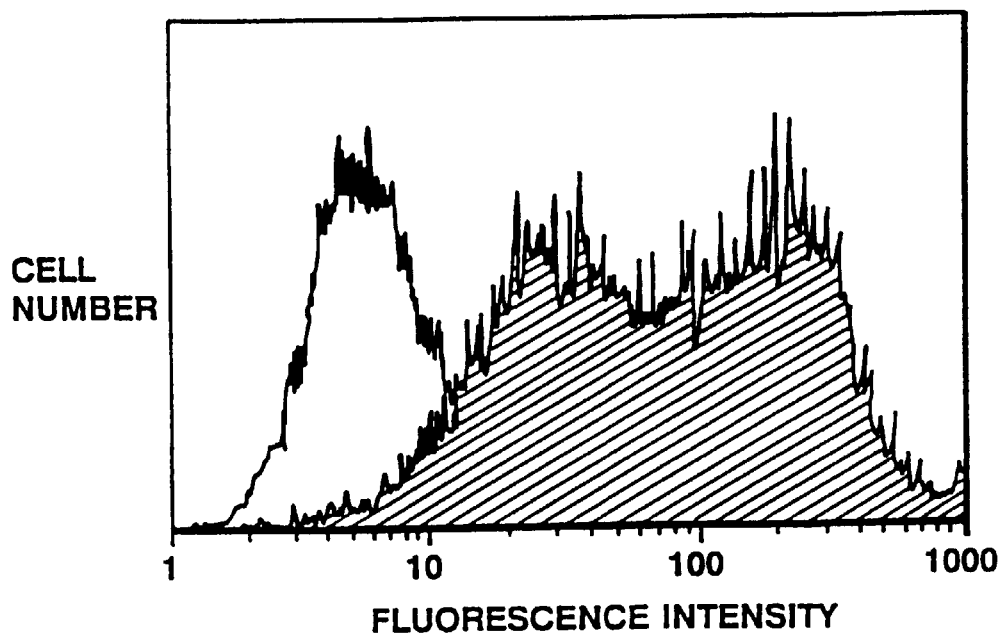
FIG. 1A shows MAG expression by transfected COS cells.

Chemical Nomenclature. The nomenclature used to describe monosaccharide constituents of oligosaccharides in the glycolipids discussed herein follows the recommendations of the IUPAC-IUB Joint Commission on Biochemical Nomenclature (*Biochem. J.* Vol. 171, p. 21 (1978); *J. Biol. Chem.* Vol. 262, p. 13 (1987)). Each monosaccharide in an oligosaccharide chain is designated by its abbreviation (as set forth in Table I, below), followed by its anomeric configuration (α or β), the position from which it is linked to the next innermost monosaccharide, and its linkage position on the ring of the next innermost monosaccharide of the chain.

For example, "Galβ1, 4Glc" designates galactose, in its β anomeric form, linked from its 1-position to the 4-position of glucose. Although not explicitly designated, all saccharides herein are in the pyranose (six-membered ring) form and are linked via their anomeric carbon (1-position for Glc, Gal, GlcNAc; 2-position for NeuAc) to the next saccharide in the chain. Branches are indicated by parentheses, such as "Galβ1, 4(Glcβ1,3)GlcNAc" which designates galactose and glucose linked from their 1-positions to the same GlcNAc ring, but at different positions (4-position and 3-position, respectively).

TABLE I

MONOSACCHARIDE CONSTITUENTS OF CARBOHYDRATES

β-D-Glucose (Glc) 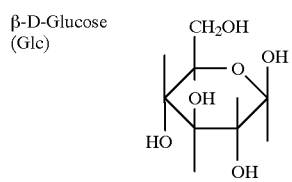  β-D-N-Acetyl-glucosamine (GlcNAc) 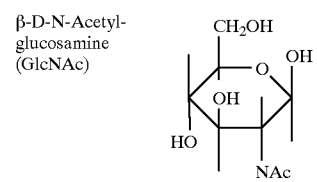

β-D-Galactose (Gal) 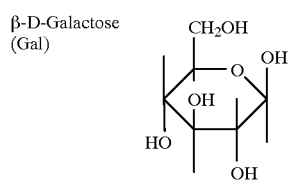  β-D-N-Acetyl-galactosamine (GalNAc) 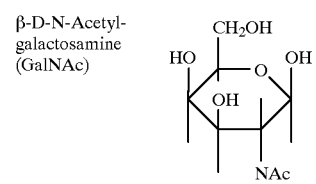

α-D-Mannose (Man) 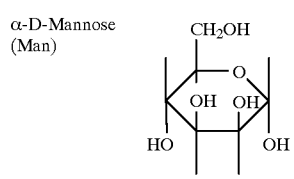  β-D-Glucuronic Acid (GlcA) 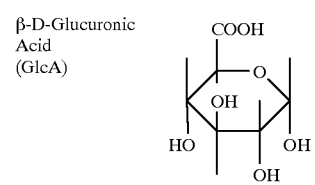

TABLE I-continued

MONOSACCHARIDE CONSTITUENTS OF CARBOHYDRATES

α-L-Fucose (Fuc)

α-D-Acetylneuraminic Acid (NeuAc)

R = —CHOH—CHOH—CH₂OH

Method for Stimulating Neuronal Growth

The invention provides a method for stimulating neuronal growth comprising contacting nerve cells with a composition comprising a therapeutically effective amount of a complex carbohydrate which has sufficient binding affinity for MAG to induce axonal growth. The complex carbohydrate has the terminal sequence:

NeuAc-Gal-A-B-C-L wherein

A is N-acetylgalactosamine,
B is galactose,
C is glucose, and
L is H or a hydrophobic group and wherein the linkage of NeuAc-Gal is NeuAc α 2, 3 Gal.

The hydrophobic group can be an aglycon. The term "aglycon" refers to alkyl, aralkyl, or aryl alcohols or phenols of glycosides. The alkyl, arakyl or aryl group from which an aglycon derives is referred to as an "aglycon group." Accordingly, the structure of the glycolipid contemplates the L moiety being an aglycon selected from the group consisting of ethanols, octanols, phenols, alkyl alcohols, aryl alcohols, and ceramides.

The complex carbohydrate that finds preferred use in this method is a glycosphingolipid. A particularly preferred form of complex carbohydrate for use in the method is a ganglioside wherein L is ceramide. However, the claimed method includes other forms of glycosphingolipids (Cuello, A., *Advances in Pharmacology*, Volume 21 (1990)), with the requirement that the hydrophilic portion (i.e. the oligosaccharide) have the terminal sequence NeuAc-Gal-A-B-C-L, wherein L is H or a hydrophobic group and wherein the linkage of NeuAc-Gal is NeuAc α 2, 3 Gal.

It was found that glycolipids having particularly advantageous pharmacologic properties in terms of binding to MAG and the ability to induce axonal growth in vitro assays had certain preferred linkages. Thus, it was found that glycolipids with a NeuAcα2,3Gal linkage between the terminal galactose of the terminal sequence and the terminal NeuAc had particularly strong and specific binding affinities for MAG. It was further found that the glycolipids which had superior binding affinities to MAG had a terminal sequence which was a gangliotetraose, which, by definition is Gal β1,3 GalNAc β1,4 Gal 4 Glc(IUPAC-IUB, *Biochem J*. Vol. 171, p. 21 (1978)).

Other particularly advantageous linkages in the glycolipid finding use in the claimed method were found to be associated with various sialic acid substitutions in the terminal sequence. For one family of compounds, the sialic acid substitutions which were found to confer the requisite binding affinity for MAG involved one to three sialic acid groups substituted onto the A moiety. The linkage which conferred MAG binding specificity was a NeuAc α2,6 GalNAc between the sialic group and A. Where A was substituted with two sialic acid groups, the linkage which conferred binding specificity on the compound was a NeuAc α2,8 NeuAc between terminal sialic acid group and the internal sialic acid group.

For another family of compounds, sialic acid substitutions which were found to confer the requisite binding affinity for MAG involved one to three sialic acid groups substituted onto the B moiety. The linkage which conferred MAG binding specificity was a NeuAc α2,3 Gal between the sialic group and B. Where B was substituted with two sialic acid groups, the linkage which conferred binding specificity on the compound was a NeuAc α2,8 NeuAc between the terminal sialic acid group and the internal sialic acid group.

Glycolipids effective in the claimed method have A and B substituted with one to three sialic acid groups having the preferred linkages between the sialic acid groups or between the sialic acid groups and the oligosaccharide in the form of gangliotetraose as described above.

Figure 2:
FIG. 2 summarizes structures of glycolipids and the ability of each to support MAG-mediated adhesion.

Glycolipids effective in the claimed method of the invention include, but are not restricted to GQ1bα, GT1b, GD1a, GT1β, and GM1b, whose structures are set forth schematically in FIG. 2. Preferred linkages in these glyolipids which are pharmacologically effective in the method of the invention for stimulating axonal growth are set forth, but not restricted to those shown in Table II below.

TABLE II

| Glycolipid | Structure |
|---|---|
| GQ1bα | NeuAc α2,3 Gal β1,3(NeuAc α2,6) GalNAc β1,4(NeuAc α2,8 NeuAc α2,3)Gal β1,4Glc β1,1'Ceramide |
| GT1b | NeuAc α2,3 Gal β1,3GalNAc β1,4(NeuAc α2,8 NeuAc α2,3) Gal β1, 4 Glc β1,1'Ceramide |
| GD1a | NeuAc α2,3 Gal β1,3 GalNAc β1, 4(NeuAc α2,3)Gal β1, 4Gl cβ1,1'Ceramide |
| GT1β | NeuAc α2,3Gal β1,3(NeuAc α2,8NeuAc α2,6)GalNAc β1, 4Gal β1,4 Glcβ1,1'Ceramide |

TABLE II-continued

| Glycolipid | Structure |
| --- | --- |
| GM1b | NeuAc α2,3 Gal β1,3 GalNAc β1,4Galβ1,4Glcβ1,1'Ceramide |

The claimed method involves contacting nerve cells with a composition comprising a therapeutically effective amount of a glycolipid. As used herein, the term "therapeutically effective amount" refers to an amount of glycolipid sufficient to effectively induce axonal growth so that regeneration of neurological tissue and neuronal connections are enhanced. Generally, the therapeutic composition is administered at a range from about 0.01 mg to about 10 mg complex carbohydrate. In addition, the particular concentration of glycolipid administered will vary with the particular nerve and injury, and its severity, as well as such factors as the age, sex, and medical history of the patient. Those of skill in the clinical arts will know of such factors and how to compensate the dose ranges of the composition accordingly.

A composition according to the method of the invention can be administered, for example, to a subject parenterally by injection or by gradual infusion over time. For example, the composition can be administered intrathecally, injected directly into the spinal cord, or directly to a neural site. Most preferably, when the nervous system dysfunction is a result of injury, administration of the composition of the invention to the subject should occur as soon as possible to the time of the injury.

Preparations for parenteral administration are contained in a pharmaceutically acceptable carrier which should be compatible with both the components of the composition and the patient. Such carriers include sterile aqueous or non-aqueous solutions, suspensions, and emulsions. Examples of non-aqueous solvents include propylene glycol, polyethylene glycol, metabolizable oils such as, olive oil, squalene or squalane, and injectable organic esters such as ethyl oleate. Liposome-based carriers are also suitable vehicles for the composition of the invention, as well as other slow-release substrates well known in the art for release of oligosaccharides.

Any of the known lipid-based drug delivery systems can be used in the practice of the invention. For instance, multivesicular liposomes (MVL), multilamellar liposomes (also known as multilamellar vesicles), unilamellar liposomes, including small unilamellar liposomes (also known as unilamellar vesicles) and large unilamellar liposomes (also known as large unilamellar can all be used so long as a sustained release rate of the encapsulated therapeutic compound can be established.

The method of making controlled release multivesicular liposome drug delivery systems is described in full in U.S. patent application Ser. Nos. 08/352,342 filed Dec. 7, 1994, and 08/393,724 filed Feb. 23, 1995 and in PCT Application Ser. Nos. US94/12957 and US94/04490, all of which are incorporated herein by reference in their entireties.

The composition of the synthetic membrane vesicle is usually a combination of phospholipids, usually in combination with steroids, especially cholesterol. Other phospholipids or other lipids may also be used. Examples of lipids useful in synthetic membrane vesicle production include phosphatidylglycerols, phosphatidylcholines, phosphatidylserines, phosphatidylethanolamines, sphingolipids, cerebrosides, and gangliosides. Illustrative phospholipids include egg phosphatidylcholine, dipalmitoylphosphatidylcholine, distearoylphosphatidylcholine, dioleoylphosphatidylcholine, dipalmitoylphosphatidylglycerol, and dioleoylphosphatidylglycerol.

In preparing vesicles containing a therapeutic agent, such variables as the efficiency of drug encapsulation, lability of the drug, homogeneity and size of the resulting population of vesicles, drug-to-lipid ratio, permeability, instability of the preparation, and pharmaceutical acceptability of the formulation should be considered. (Szoka, et al., *Annual Reviews of Biophysics and Bioengineering*, 9:467, 1980; Deamer, et al., in *Liposomes*, Marcel Dekker, New York, 1983, 27; Hope, et al., *Chem. Phys. Lipids*, 40:89, 1986).

A lipid-based drug delivery system incorporating the therapeutic compound can be delivered to the central nervous system as a single dose, for instance, via an epidural catheter. For example, a lipid-based drug delivery system is injected as a single dose into the epidural space surrounding the spinal cord using a small gauge needle so that emplacement of a catheter is avoided. Preferably, an 18 gauge to 25 gauge needle is used.

Aqueous pharmaceutical carriers include water, alcoholic/aqueous solutions, emulsions or suspensions, including saline and buffered media. Parenteral vehicles include sodium chloride solution, Ringer'dextrose, dextrose and sodium chloride, lactated Ringer', or fixed oils. Preservatives and other additives may also be present such as, for example, antimicrobials, anti-oxidants, chelating agents, and inert gases and the like. Preferred as a carrier vehicle is artificial cerebrospinal fluid.

Method for Identifying Compounds

The invention provides a method for identifying a compound which inhibits myelin-associated glycoprotein (MAG) inhibition of axonal growth. Such compounds are capable of stimulating axonal growth when brought in contact with nerve cells by virtue of their ability to inhibit MAG. The claimed method comprises contacting the compound with MAG under conditions which allow MAG and the compound to bind. The method detects the binding of the compound with MAG, as well as characterizing the affinity between the compound and MAG, the strength of the binding, and the compounds ability to inhibit (i.e. diminish) MAG inhibitory activity.

Compounds which can be screened using the claimed method are glycolipids, particularly gangliosides which are found in nervous system tissue. Gangliosides represent a large and varied family of sialic acid containing cell surface glycosphingolipids (C. L. M. Stults, C. C. Sweeley, B. A. Macher, *Methods Enzymol.* 167 (1989); R. K. Yu, M. Saito, in *Neurobiology of glycoconjugates*, R. U. Margolis and R. K. Margolis, Eds. (Plenum Press, New York, 1989), p.1). Other compounds which can be screened using the claimed method include, but are not restricted to, proteins (e.g., monoclonal antibodies), as well as oligosaccharides or glycosides with hydrophobic aglycons.

The claimed method is operable for contacting compounds with MAG under soluble or surface-bound conditions. Thus, both the candidate test compound and MAG can be screened for binding between both moieties when both are in soluble phase. Under such conditions, detection of the binding between MAG and the test compound is facilitated by the use of detectably labeled compounds, or by the use of detectably labeled MAG. Preparation of detectably labeled compounds, and in particular, detectably labeled MAG or other proteins; and detectably labeled glycosides or gangliosides, involves procedures well known in the art (*Current Protocols in Molecular Biology*, ed. Ausubel, F. M. et al., publ., John Wiley & Sons, Inc., 1994—Section 10.18 for proteins; Section 17 for glycolipid compounds). Accordingly, MAG or candidate compounds can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to MAG, and test compounds, or will be able to ascertain such, using routine experimentation.

Methods for measuring the binding affinity between a test compound and MAG or merely the binding itself are well known in the art, and involve methods for detecting binding between soluble molecules, such as equilibrium dialysis or precipitation of molecular complexes followed by filtration (M. A. Lehrman, et al., *J. Biol. Chem.* Vol. 261, p. 7412 (1986); R. L. Hudgin, et al., *J. Biol. Chem.* Vol. 249, p. 5536 (1974); R. L. Schnaar, et al. *Prog. Brain Res.* Vol. 101, p. 185 (1994)), and methods for detecting binding of a soluble molecule to a molecule immobilized on a plastic surface (K. Karlsson and N. Stromberg, *Methods Enzymol.* Vol. 138, p. 220 (1987); L. K. Needham and R. L. Schnaar, *Proc. Natl. Acad. Sci. USA*, Vol. 90, p. 1359 (1993); R. L. Schnaar, *Methods Enzymol.* Vol. 138, p. 220 (1987)) or on an affinity matrix (R. K. Merkle and R. D. Cummings, *Methods Enzymol.* Vol. 138, p. 232 (1987); D. F. Smith and B. V. Torres, Methods *Enzymol.* Vol. 179, p. 30 (1989)).

In an embodiment of the method of the invention for screening candidate compounds, MAG is provided in its transmembrane form on the surface of carrier cells which were transfected with cDNA encoding MAG. The untransfected carrier cells do not normally bind to nerve cell carbohydrates. The claimed method involves contacting the transfected cells with various test compounds under conditions which allow MAG on the surface of the cells and the compound to bind, and detecting the binding of the candidate test compound as compared to untransfected control cells or cells transfected with a control cDNA (see Examples below). The compound may be detectably labeled. Binding can be detected using various standard receptor-ligand binding measurment techniques well-known to those skilled in the art.

A preferred embodiment of the claimed method involves attaching the test compound to a solid surface. As described in Example 2 below, the solid surface to which the compound was attached was contacted with MAG-transfected cells under conditions which allow MAG and the compound to bind. A test compound, in the form of a ganglioside, was adsorbed to a microwell surface as an artificial membrane monolayer of phosphatidylcholine and cholesterol. Other methods are known in the art for attaching compounds, typically complex carbohydrates to surfaces such as polystyrene, polyvinylcarbonate, or polyacrylamide (R. L. Schnaar in *Neoglycoconjugates, Preparation and Application*, Y. C. Lee and R. T. Lee, eds., p. 425, 1994).

Binding between MAG and the test compound attached to the solid surface is measured by detecting the adherence of the transfected cells to the solid surface as compared to adhesion of transfected cells to the solid surface lacking the test compound. Cell adhesion can be typically measured and quantitated by measuring enzymatic activity, such as lactate dehydrogenase in the lysate of the cells adhered to the solid surface.

As described in Examples 2 and 3 below, different nerve cell carbohydrate compounds were mounted, immobilized, or attached on inert surfaces. Transfected carrier cells which express MAG on their surface were placed in contact with different carbohydrates, and cell adhesion to the surface was measured.

Using this embodiment of the claimed method, cells with MAG expressed on their surface showed highly specific, superior binding to α2,3 linked sialic acid on a Galβ1, 3GalNAc core structure of a glycolipid ganglioside. After removing non-adherent cells from the plastic surface, the claimed method detected binding of MAG with the compound by measuring or quantitating the binding of tranfected cells which remained on the surface. The affinity of a soluble compound which inhibits MAG-mediated inhibition of nerve growth is preferably $10^6$ M$^{-1}$ or greater, more preferably $10^8$ M$^{-1}$ or greater, although compounds with affinities of $10^4$ M$^{-1}$ may be therapeutically effective.

Certain glycolipids identified by the method of the invention are known to be expressed on myelinated neurons in vivo (R. K. Yu, M. Saito in *Neurobiology of Glycoconjugates*, R. U. Margolis and R. K. Margolis, eds., Plenum Press, New York, 1989). The specificity of carbohydrate binding, as determined by the claimed method, defined a set of structurally related glycolipids as ligands for MAG. When used in the method of the invention for stimulating neuronal growth, these structurally related glycolipids have the property of enhancing axonal growth when brought into contact with nerve cells. In the present invention it was found that these structurally related compounds are glycolipids having the terminal sequence:

NeuAc-Gal-A-B-C-L wherein
A is N-acetylgalactosamine,
B is galactose,
C is glucose, and
L is a hydrophobic group and
wherein the linkage of NeuAc-Gal is NeuAc α 2, 3 Gal.

Using in vitro assays of nerve cell growth, as described in the examples below, the compounds identified by the claimed method can inhibit MAG inhibition of axonal growth. The compounds which were bound to MAG are useful for inhibiting MAG-nerve cell binding or adhesion, and, thereby, are inhibitors of MAG inhibition of axonal growth. Accordingly, the compounds identified by the invention find use in another aspect of the invention, namely, a method for stimulating neuronal growth.

The following examples are intended to illustrate but not limit the invention. While they are typical of those that might be used, other procedures known to those skilled in the art may alternatively be used.

EXAMPLES

Example 1

MAG-Transfected COS Cells cDNA encoding MAG was cloned into the mammalian expression vector pCDM8 in the correct orientation or in the reverse orientation (control). Plasmids containing cDNA encoding the long form of MAG were constructed by excising the full length cDNA from pGEM-L-MAG (obtained from Dr. B. D. Trapp, Cleveland Clinic, Cleveland, Ohio ) using ApaI and inserting the fragment in either the forward (pCDM8-MAG) or reverse orientation (control) into the expression vector pCDM8 using BstXI/EcoRI adapters (Invitrogen, San Diego, Calif.). [B. Seed, Nature 329, 840 (1987)] The size of the MAG expression product was confirmed by in vitro translation (TnT system, Promega, Madison, Wis. ),resulting in a protein of approximately 70 kD produced by the forward construct only. Sequencing of 600 bp from the 3' end of the insert confirmed the presence of rat MAG (long form) cDNA. COS-1 cells were transfected with pCDM8-MAG or the reverse construct, using a high efficiency DEAE-dextran procedure [B. Seed and A. Aruffo, Proc. Natl. Acad. Sci. U.S.A. 84, 3365 (1987)]. After 60 h, cells were detached from plates in a phosphate-buffered saline solution (308 mM NaCl, 16 mM $Na_2HPO_4$, 3 mM $KH_2PO_4$, 5.4 mM Kcl, 1 mM EDTA), collected by centrifugation and resuspended in Dulbecco's phosphate-buffered saline. Expression of MAG was confirmed immunocytochemically using a Coulter Epics flow cytometer (Coulter Corp., Hialeah, Fla.) By incubating $4\times10^5$ cells for 30 min at 4° C. with 30 µg/ml anti-MAG antibody (mAb 513, Boehringer-Mannheim, Indianapolis, Ind.) in 30 µl phosphate-buffered saline containing 20 mg/ml bovine serum albumin. Cells were washed by centrifugation and stained for 30 min at 4° C. with a 1:100 dilution of phycoerythrin-conjugated polyclonal goat anti-mouse IgG F(ab)' (TAGO, Inc., Burlingame, Calif.). At least 5,000 cells were evaluated for each flow cytometric profile. Background fluorescence was defined using an irrelevant mouse IgG1 isotypic control antibody (Coulter Corp., Hialeah, Fla.).

Plasmids were transfected into COS-1 cells using a highly efficient DEAE-dextran procedure. As shown in FIG. 1 (A), MAG expression was confirmed by flow cytometric analysis of intact cells stained with mAb 513, which binds to a conformational epitope in the third extracellular Ig-like domain of MAG (T. Fahrig, R. Probstmeier, E. Spiess, A. Meyer-Franke, F. Kirchoff, et al., Eur. J. Neurosci. 5, 1118 (1993).). The large majority of the MAG-transfected COS cells bound mAb 513, leading to relative fluorescence levels that were 5- to 40- fold above background (FIG. 1A). In contrast, COS cells transfected with control plasmid were indistinguishable from background, as were MAG- or control-plasmid transfected COS cells stained with an irrelevant isotype-matched control antibody (data not shown).

Example 2

Adherence of MAG-Transfected COS Cells to Microwell Surfaces on which Gangliosides Were Adsorbed In order to determine the binding affinity of MAG to glycolipids, MAG-mediated cell adhesion to surfaces comprising various purified glycolipids was tested.

MAG-or control-transfected COS cells were collected from plates 36–48 h after transfection, as described above, and suspended at a concentration of $2\times10^5$ cells /ml in Hepes-buffered DMEM containing 1 mg/ml BSA. Ganglioside GT1b (obtained from EY Labs, San Mateo, Calif.) was evaporated from storage solvent (chloroform-methanol-water (4:8:3)) and resuspended at the desired concentrations in ethanol containing 1 µM phosphatidylcholine and 4 µM cholesterol. An equal volume of water was added, 50 µl were placed into microwells of a 96-well Serocluster plate (Costar, Cambridge, Mass.), and plates incubated uncovered for 75–120 min to allow efficient lipid absorption (C. C. Blackburn, et al., J. Biol. Chem. 261:2873, 1986). Plates were washed with water, pre-blocked by addition of 100 µl/well of Hepes-buffered DMEM containing 1 mg/ml BSA for 10 min at 37° C., and 200 µl of cell suspension were added. Plates were incubated for 10 min at 4° C. to allow cells to settle, then were transferred to 37° C. for 50 min. To remove non-adherent cells after the incubation, the plate was immersed, upright, in a vat of PBS, inverted, and placed in an immersed custom-designed Plexiglas box which was sealed with a gasket to exclude air. The inverted plate in its fluid-filled chamber was placed in a centrifuge carrier and centrifuged at 24×g to gently remove non-adherent cells. The box was again immersed in a vat of PBS and the plate was removed, righted (while immersed), surface fluid removed by aspiration, 20 µl of 10% Triton X-100 was added, mixed, and 80 µl/well removed to a fresh 96-well plate. Cell adhesion was quantitated by measuring lactate dehydrogenase (LDH) activity in the cell lysate after addition of 120 µl of 0.1M potassium phosphate buffer pH 7.0 containing 0.7 mM NADH and 4.7 mM pyruvate. The decrease in absorbance at 340 nm as a function of time was measured simultaneously in each well using a Molecular Devices UV multiwell kinetic plate reader.

Figure 1B:
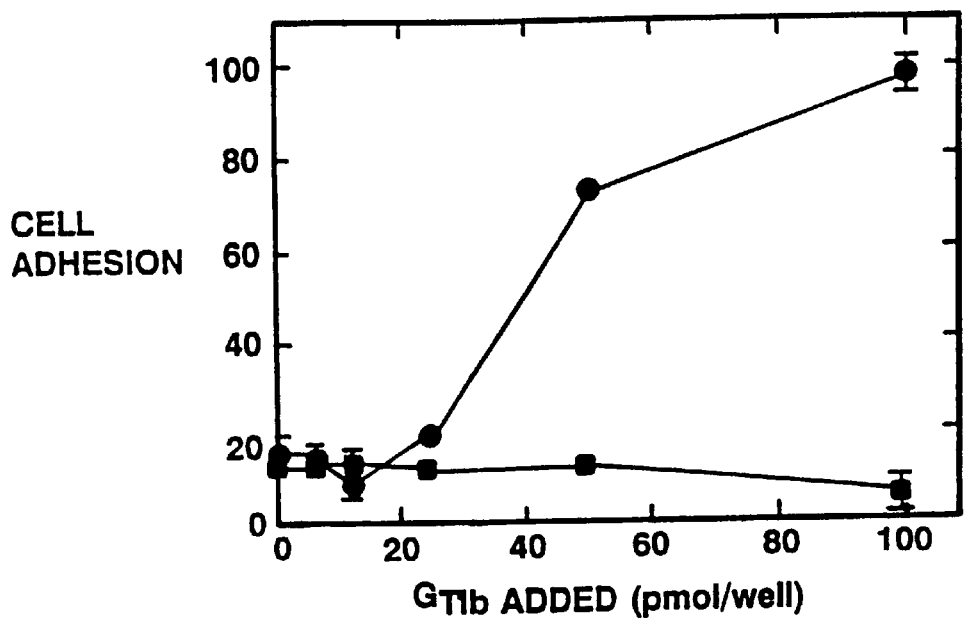
FIG. 1B shows the adherence of MAG-transfected COS cells to microwell surfaces to which ganglioside GT1b was adsorbed.

FIG. 1(B) shows measurement of adhesion of MAG-transfected COS cells to microwells adsorbed with the indicated amounts of GT1b. Adhesion of MAG-transfected (circles) and control-transfected (squares) COS cells to each amount of GT1b was measured. All wells (including those with no GT1) were co-absorbed with 25 pmol/well phosphatidylcholine and 100 pmol/well cholesterol. Cell adhesion was reported as LDH activity ($\Delta A340/min\times10^3$). Values are the mean ±SE of quadruplicate determinations.

It was found that the MAG-transfected COS cells adhered in a concentration-dependent manner to microwell surfaces on which the ganglioside GT1b was absorbed as an artificial membrane monolayer of phosphatidylcholine and cholesterol (FIG. 1B). MAG-transfected COS cells did not bind to the artificial membrane lacking GT1b, and in control-transfected COS cells did not bind to GT1b-absorbed to control surfaces. Typically, 30–40% of the MAG-transfected cells added to GT1b-absorbed well adhered under these conditions, while <8% bound to control surfaces. These data demonstrated the ability of a purified endogenous neuronal glycoconjugate, ganglioside GT1b, to support MAG-mediated cell adhesion, and defined conditions for subsequent carbohydrate specificity studies.

Figure 1C:
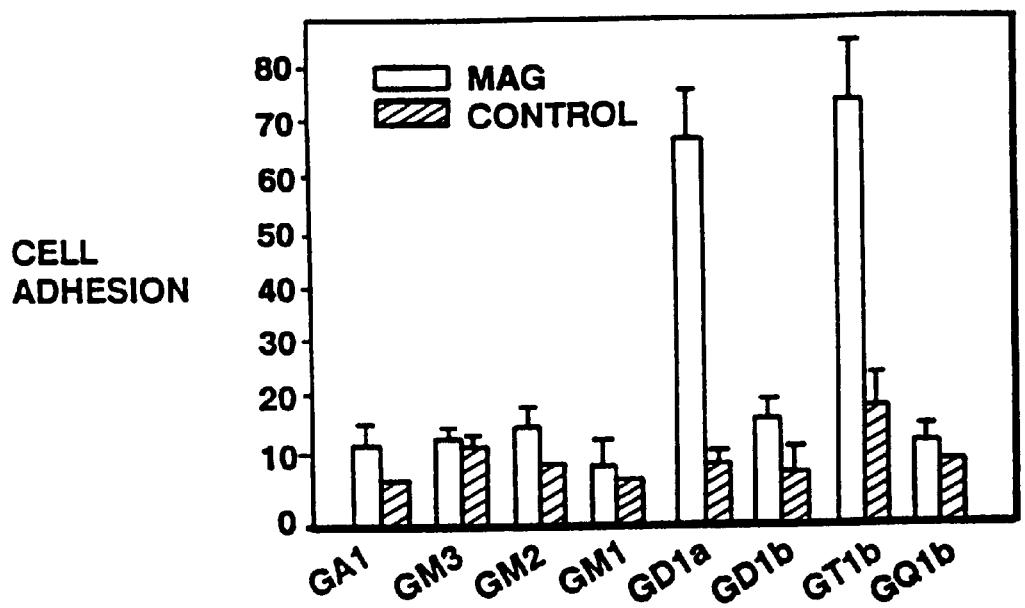
FIG. 1C shows the adherence of MAG-transfected COS cells to microwell surfaces to which various gangliosides were adsorbed.

FIG. 1(C) shows MAG-mediated adhesion of transfected COS cells to major brain gangliosides. The indicated gangliosides were adsorbed at 50 pmol/well as in FIG. 1(B).

Adhesion of MAG-transfected (solid bars) and control-transfected (hatched bars) COS cells to each ganglioside was measured. Cell adhesion was reported as LDH activity ($\Delta A340/min \times 10^3$). Values are expressed as the mean ±SE of quadruplicate determinations. GA1, GM1, GD1a, and GD1b were from EY Labs (San Mateo, Calif.); GM3 was from Sigma (St. Louis, Mo.); GQ1b was from Accurate Chemical Co. (Westbury, N.Y.); and GM2 was purified from human Tay-Sachs brain according to the method of L. Svennerholm and P. Fredman (*Biochim. Biophys. Acta* Vol. 617, p. 97, 1980). The efficiency and stability of adsorption of different gangliosides was comparable (C. C. Blackburn, P. Swank-Hill, R. L. Schnaar, *J. Biol. Chem.* 261:2873, 1986).

Figure 1D:
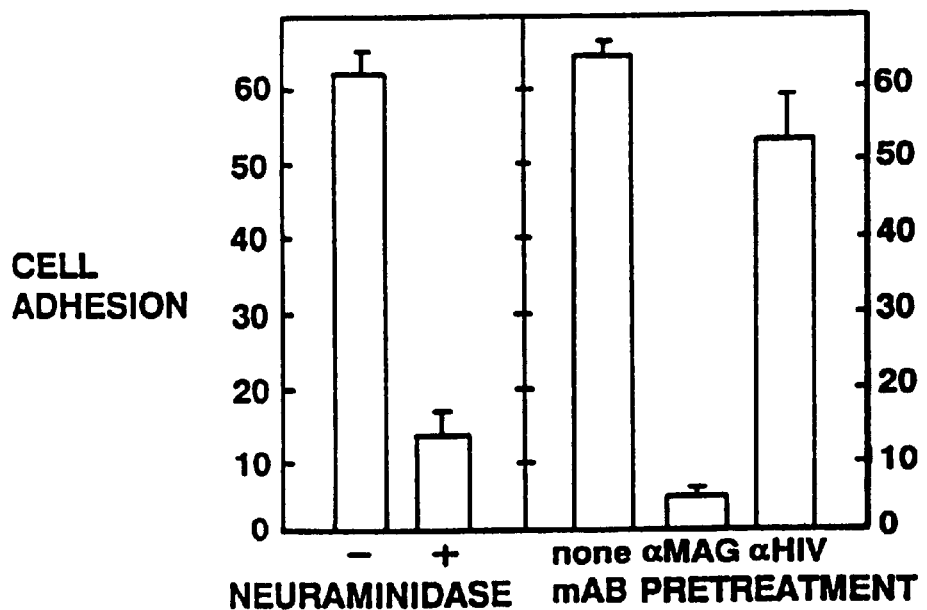
FIG. 1D shows the effects on the adherence of MAG-transfected COS cells of pre-treating microwell surfaces adsorbed with GT1b ganglioside with neuraminidase; or the effect on the adherence of the cells to microwell surfaces adsorbed with GT1b ganglioside of pretreating MAG-transfected COS cells with mAb513.

To confirm that MAG-mediated ganglioside adhesion was dependant on the terminal sialic acid, microwells absorbed with GT1b were incubated with Vibro cholerae neuraminidase, which cleaves the NeuAc $\alpha 2,3$ Gal bond on the terminal galactose and the NeuAc $\alpha 2,8$ NeuAc bond, but not the NeuAc $\alpha 2,3$ Gal bond on the internal galactose. Neuraminidase-treated microwells did not support adhesion of MAG-transfected cells, whereas control-treated microwells supported adhesion (FIG. 1D). Pretreatment of MAG-transfected COS cells with mAb 513, which blocks MAG-liposome binding to neurons in culture and inhibits oligodendrocyte-neuron binding (R. Sadoul, T. Fahrig, U. Bartsch, M. Schachner, *J. Neurosci. Res.* 25, 1(1990), M. Poltorak, R. Sadoul, G. Keilhauer, C. Landa, T. Fahrig, et al., *J. Cell Biol.* 105:1893, 1987); P. W. Johnson, W. Abramow-Newerly, B. Seilheimer, R. Sadoul, M. B. Tropak, et al., *Neuron* 3:377, 1989), blocked MAG-medicated cell adhesion to GT1b-absorbed surfaces (FIG. 1D). Treatment of the same cells with an isotype matched control antibody had no inhibitory effect. These data are consistent with the interpretation that the site on MAG responsible for neuronal cell adhesion is the ganglioside recognition site.

Example 3

Structure Function Studies of Glycolipid Binding to MAG

Each of 19 glycolipids was tested at a variety of concentrations for its ability to support adhesion of MAG-transfected COS cells as in FIG. 1B. In FIG. 2, five structures which supported cell adhesion are shown in the left column, with the amount required to support half-maximal cell adhesion (pmol/well). Structures which did not support any cell adhesion are shown at the far right, tested at amounts as high as 100–200 pmol/well.

Glycosphingolipids not previously listed were obtained from the indicated sources. GQ1bα was obtained according to the method of Hirabayashi, Y., et al. (*J. Biol. Chem.* 267(18):12973, 1992.) GM1b was prepared according to the method of Ariga, T., et al. (*J. Lipid Research* 28:285, 1987). 2,6SnLc (sialylneolac-totetraosylceramides) and SLe* (sialyl Lewis x) were obtained from Glycomed, Inc., Alameda, Calif. GD3 and sulfatides were from Matreya, Pleasant Gap, PA. SGGL (3-sulfoglucuronylneolacto tetraosylceramide) was prepared from bovine cauda equina (L. K. Needham, R. L. Schnaar, *J. Cell Biol.* 121:397, 1993). Note: NeuAc-NeuAc bonds are all $\alpha 2,8$. Other NeuAc bonds are as noted in the key.

GT1, βGQ1α, GT1, βGQ1α, and GM1α were synthesized as described below in Example 5.

Among the major brain gangliosides, only GT1b and GD1a supported MAG-mediated cell adhesion (FIGS. 1C and 2). Adhesion required a terminal NeuAcα2,3Gal determinant (compare GD1a to GM1 and GM1b to GA1), but is abrogated by the presence of an additional terminal α2,8-linked sialic acid (compare GT1b to GQ1b). Notably, NeuAcα2,3Gal presented on a different saccharide core (as in GM3 or 2,3SnLc) did not support adhesion. This observation, along with the enhanced binding of GD1a or GT1b compared to GM1b, indicated that the gangliotetraose core was recognized along with the sialic acid on the internal galactose residue.

Figure 3:
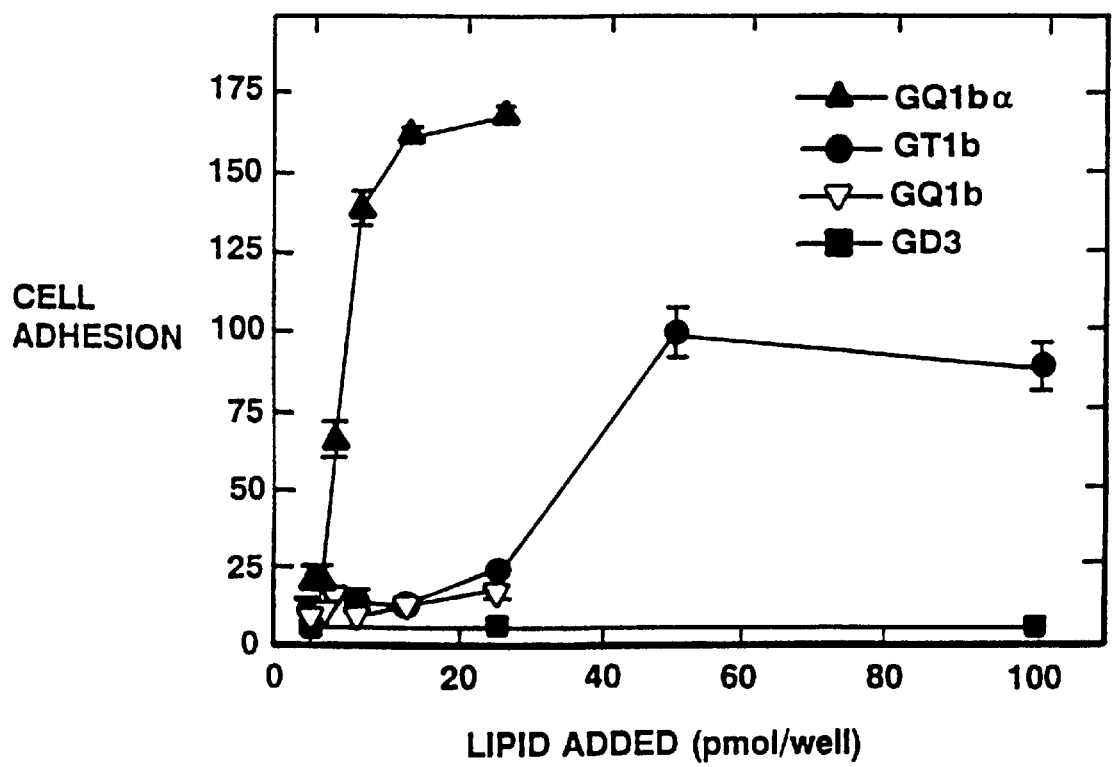
FIG. 3 shows the adherence of MAG-transfected COS cells to microwell surfaces to which various gangliosides were adsorbed.
Figure 4:
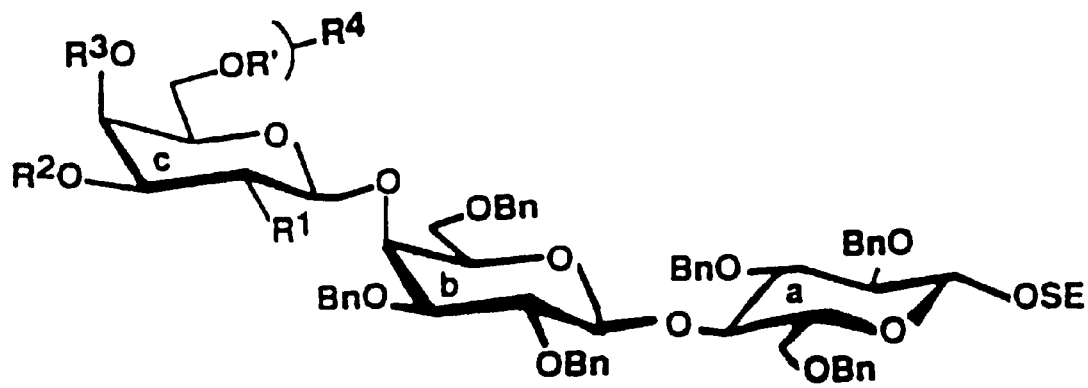
FIG. 4 shows the chemical structure of Compounds 1, 2 and 3 of Example 5.
Figure 5:
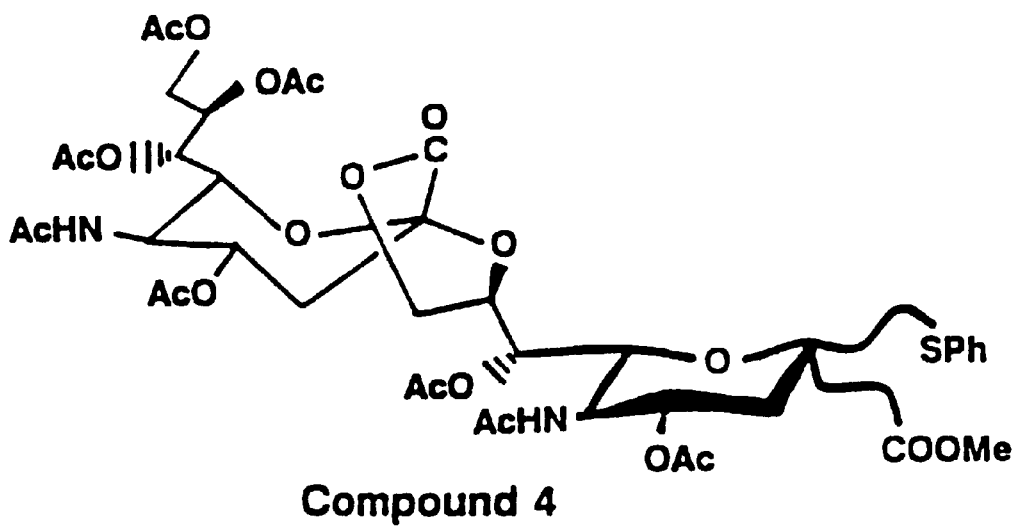
FIG. 5 shows the chemical structure of Compound 5 of Example 5.
Figure 6:
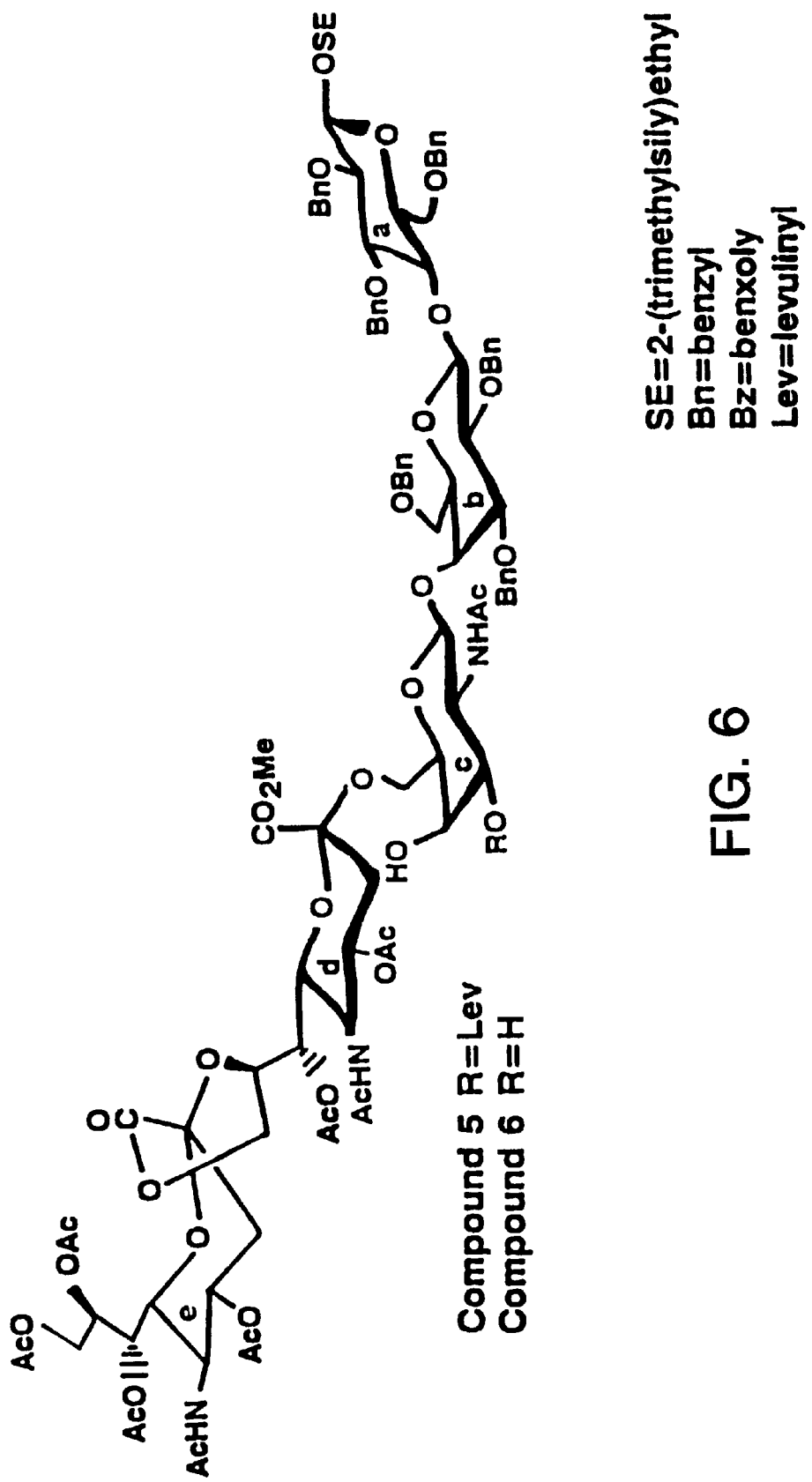
FIG. 6 shows the chemical structure of Compounds 5 and 6 of Example 5.
Figure 7:
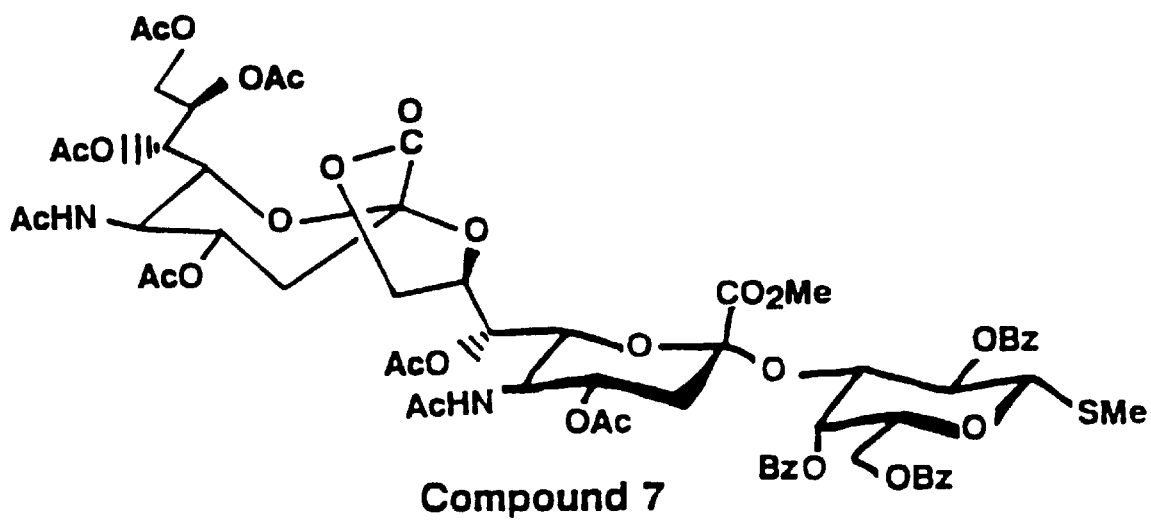
FIG. 7 shows the chemical structure of Compound 7 of Example 5.
Figure 9:
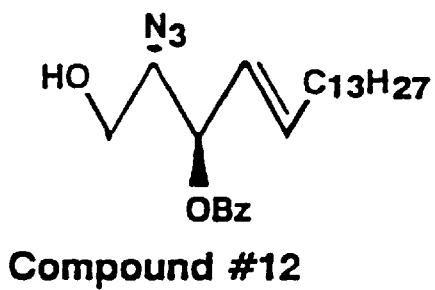
FIG. 9 shows the chemical structure of Compound 12 of Example 5.
Figure 8:
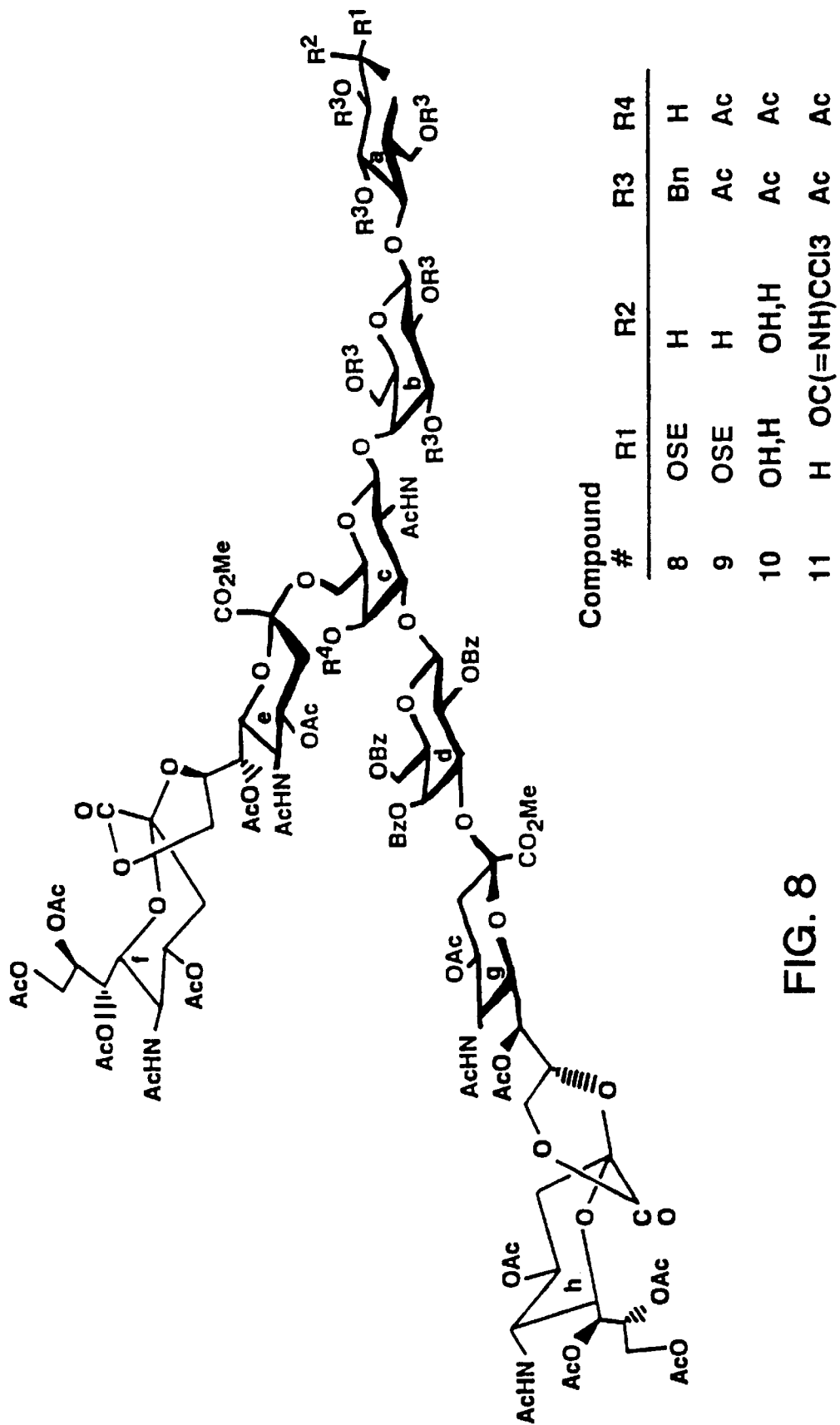
FIG. 8 shows the chemical structure of Compounds 8, 9, 10 and 11 of Example 5.
Figure 10:
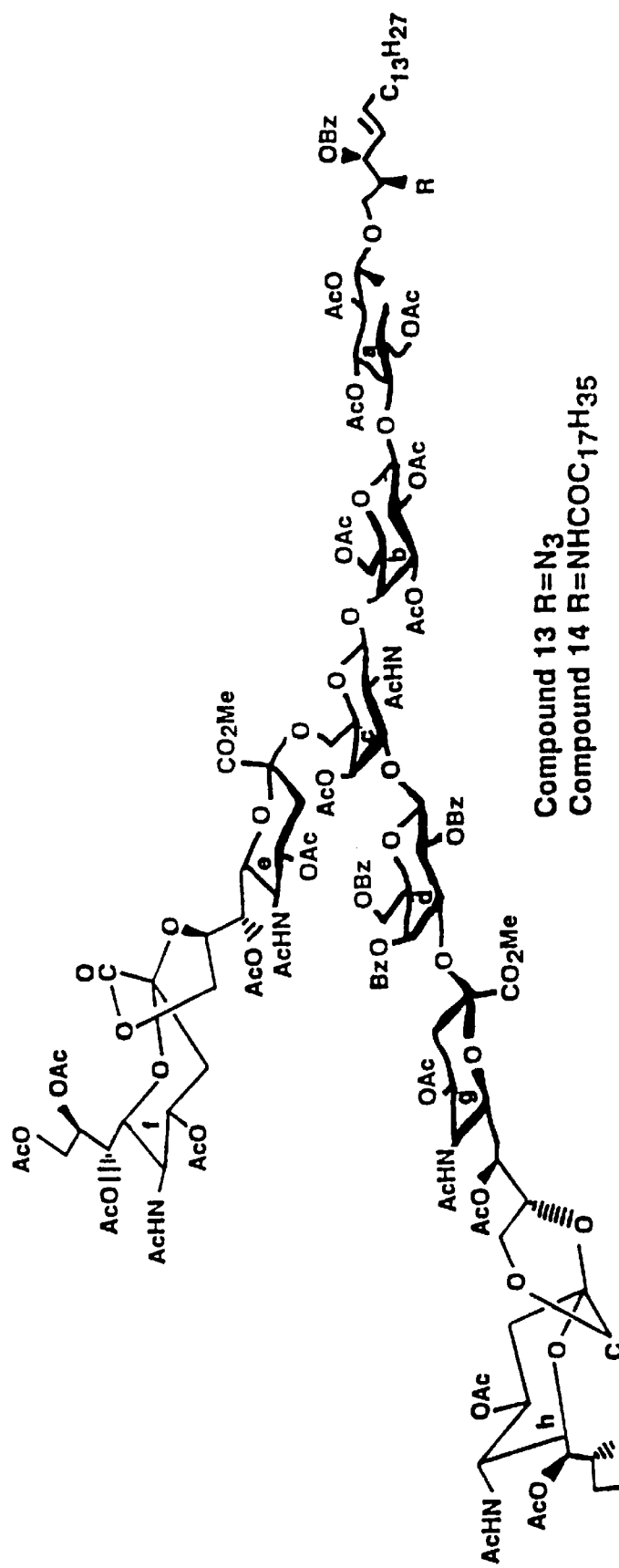
FIG. 10 shows the chemical structure of Compounds 13 and 14 of Example 5.
Figure 11:
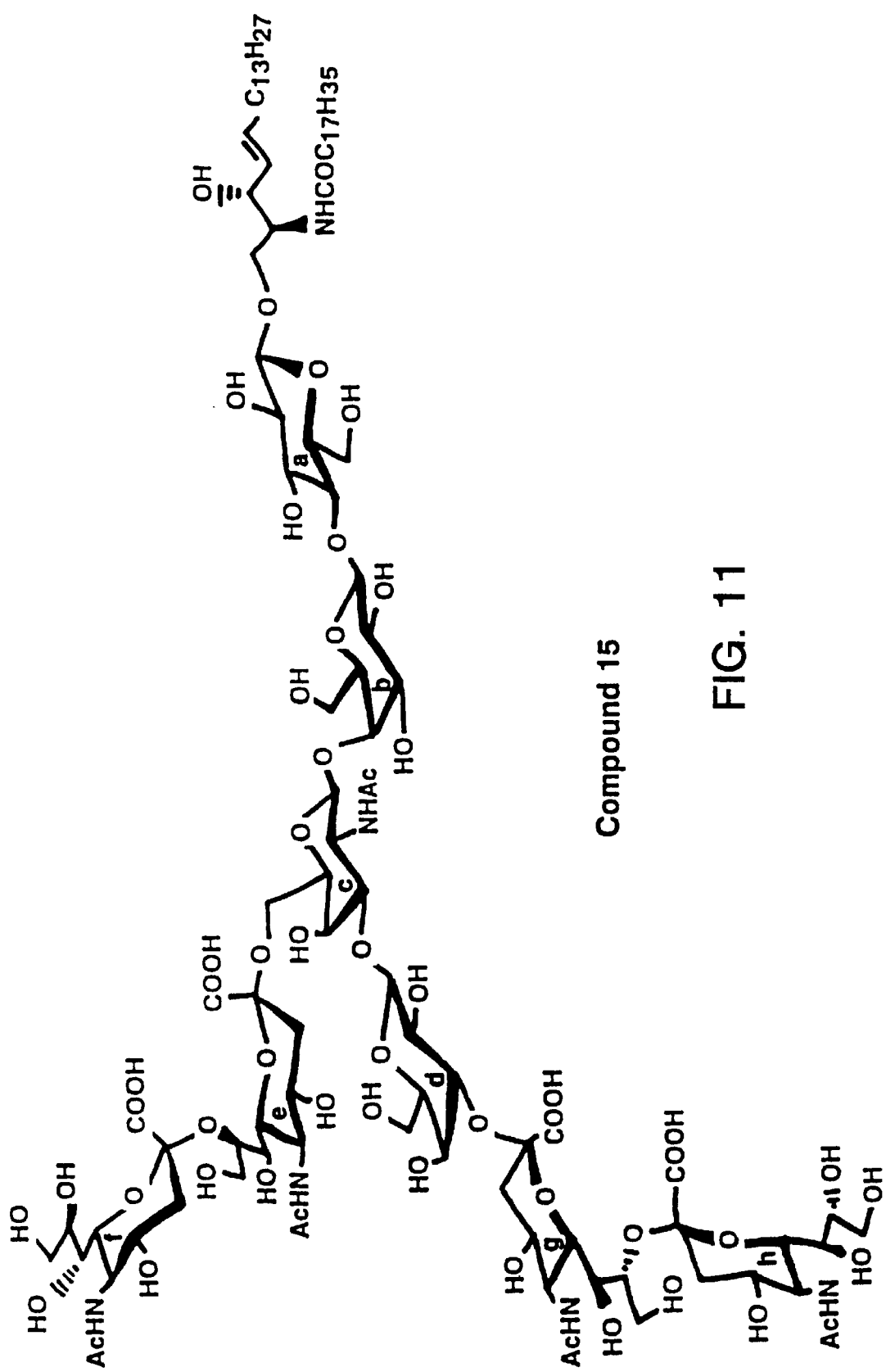
FIG. 11 shows the chemical structure of Compound 15 of Example 5.
Figure 12:
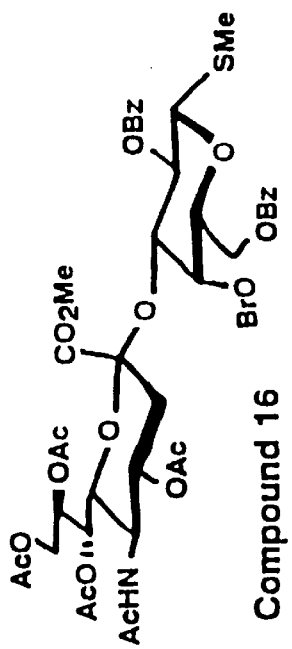
FIG. 12 shows the chemical structure of Compound 16 of Example 5.
Figure 13:
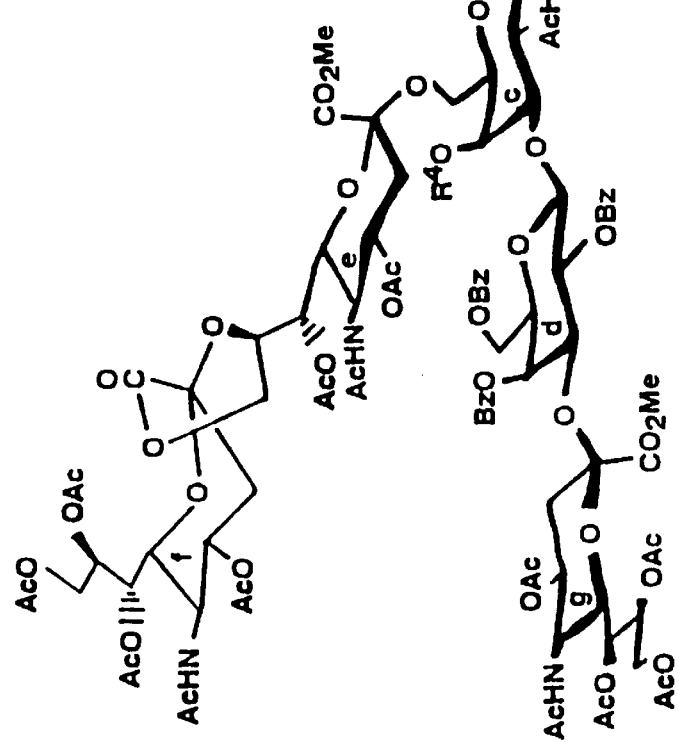
FIG. 13 shows the chemical structure of Compounds 17, 18, 19, and 20 of Example 5.
Figure 14:
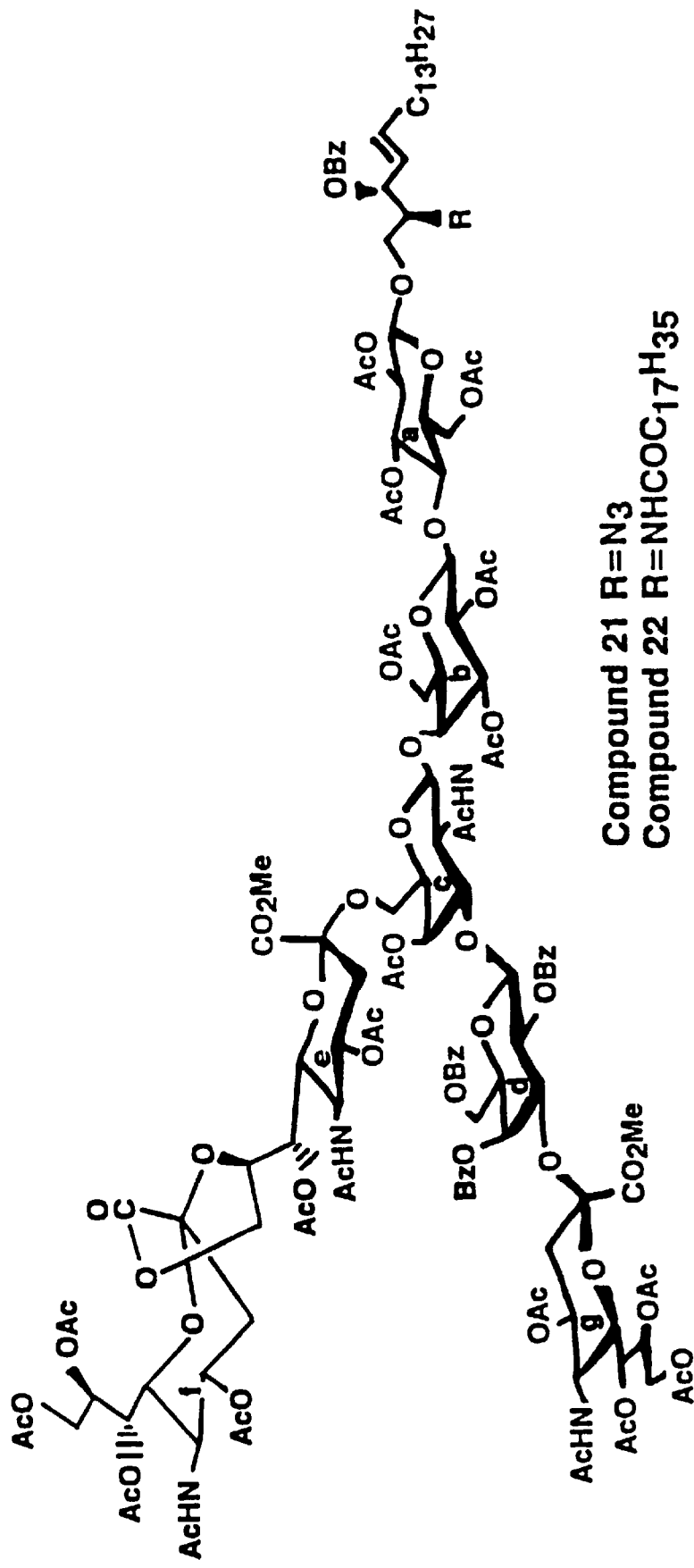
FIG. 14 shows the chemical structure of Compounds 21 and 22 of Example 5.
Figure 15:
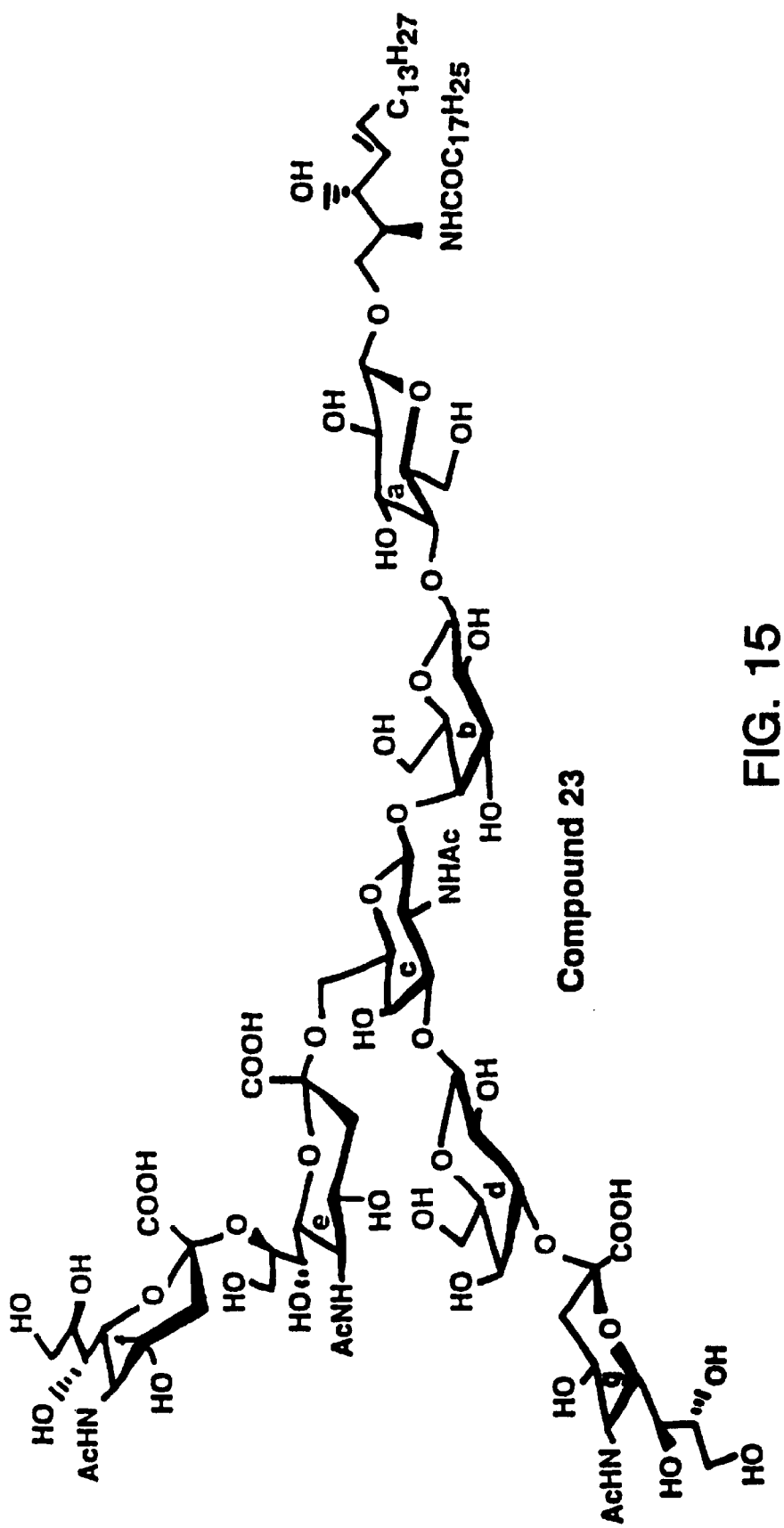
FIG. 15 shows the chemical structure of Compound 23 of Example 5.

A surprising additional finding arose from ganglioside structure-function studies. Quantitatively minor gangliosides termed "Chol-1" gangliosides, are the target of antibodies highly specific for cholinergic neurons throughout the nervous system (R. T. Jones, J. H. Walker, P. J. Richardson, G. Q. Fox, V. P. Whittaker, *Cell Tissue Res.* 218:355, 1981; Y. Hirabayashi, T. Nakao, F. Irie, V. P. Whittaker, K. Kon, et al., *J. Biol. Chem.* 267:12973, 1992; P.Feretti, E. Borroni, *J. Neurochem.* 46,1888, 1986). Chol-1 gangliosides are related to the major brain gangliosides but have additional sialic acid(s) linked α2,6 to the GalNAc in the gangliotetarose core. Chol-1 antibodies do not cross react with any proteins on Western blots, yet bind to gangliosides on cholinergic neurons in organisms ranging form Torpedo to man. Their role in cholinergic neuronal function is unknown. GQ1bα was 8-fold more potent than GT1b at supporting MAG-mediated cell adhesion (FIGS. 2 and 3). FIG. 3 demonstrates enhanced support of MAG-transfected COS cell adhesion by the glycolipid GQ1bα. Microwells were absorbed with various amounts of the indicated gangliosides, and adhesion of MAG-transfected COS cells was performed as described in FIG. 1B. Cell adhesion was reported as LDH activity ($\Delta A340/min \times 10^3$). Values are expressed as the mean ±SE of quadruplicate determinations.

GQ1α also supported adhesion of a greater percentage of MAG-transfected COS cells (70–80% of the cells added) compared to other gangliosides tested, suggesting that a lower cell surface concentration of MAG was sufficient to support COS cells to GQ1bα compared to GT1b (FIG. 3) or other gangliosides. Binding of MAG-transfected COS cells to GQ1α was completely blocked by pretreatment of the absorbed ganglioside with V. Cholerae neuraminidase (data not shown). The enhanced ability of GQ1bα to support MAG-mediated cell adhesion was unanticipated for two reasons. First, α2,6-linked sialic acids by themselves do not support MAG-Fc binding under conditions where α2,3-linked sialic acids support binding (S. Kelm, A. Pelz, R. Schauer, M. T. Filbin, T. Song, et al., *Curr.Biol.* 4:965, 1994). Second, Chol-1 gangliosides are thought to be restricted to cholinergic neurons, while myelination is not neurotransmitter-restricted.

Considered together, the ganglioside binding data in FIG. 2 indicated that an α2,3 NeuAc residue on the terminal galactose of a gangliotetraose core was required for MAG binding, but that additional sialic acid residues at each of the two other known sites of sialylation (α2,6 to the GalNAc and α2,3 to the internal Gal) contributed meaningfully and advantageously to increased binding affinity. The lack of any MAG-mediated cell adhesion to other, closely related ganglioside structures indicated a level of ganglioside binding specificity rivaled only by Cholera toxin, which binds to GM1 (J. Holmgren, *Infect. Immun.* 8:851, 1973). These findings which concern the specificity and strength of glycolipid binding to MAG, and the loss of that sensitivity associated with the binding of MAG to a monoclonal antibody directed against a neuronal cell adhesion epitope support the advantage of the claimed glycolipids and claimed methods of use for mediating MAG-neuron interactions so as to inhibit MAG-mediated inhibition of neurite outgrowth, thereby inducing neurite or axonal growth after injury to neurons.

Example 4

Effects of Identified Compounds on Axon Growth

The ability of the compounds identified by the method of the invention to inhibit myelin-associated glycoprotein inhibition of axon growth is demonstrated using in vitro assays:

A. In vitro assay for ganglioside effects on MAG-inhibition of neurite outgrowth by observing neurite extension from NG108-15 cells on MAG adsorbed to plastic surfaces. [following the method of McKerracher, L., et al., *Neuron,* 13:805, 1994] NG108-15 is a neuroblastoma-glioma hybrid cell line which can undergo morphological (neurite extension) and biochemical (increased choline acetyltransferase) differentiation; these cells can synthesize and store acetylcholine, express neurotransmitter receptors, and form functional synapses with each other and with muscle cells in culture.

To study the effect of compounds on the inhibition of neurite outgrowth by myelin-associated glycoprotein (MAG), NG108-15 cells are cultured in DMEM supplemented with calf serum, hypoxanthine, aminopterin, and thymidine, then differentiated with 1 mM theophylline and 10 $\mu$M prostaglandin El (PGE1) in the above medium for 48 hours prior to assay. Multiwell tissue culture dishes pre-coated with 15 $\mu$g/mL poly-D-lysine then adsorbed with 4 $\mu$g/well purified rat central nervous system myelin-associated glycoprotein (CNS MAG) are pre-treated with micromolar concentrations of gangliosides as micelles or in liposomes, millimolar concentrations of ganglioside oligosaccharides, or with corresponding concentrations of control glycolipids and oligosaccharides. Subsequently, the "primed" NG108-15 cells are added to the various test substrata at a density of 1000 cells/well, cultured for 24 hours, then fixed with 4% paraformaldehyde in 0.1 M phosphate buffer and stained with cresyl violet. The fixed cells are scored microscopically for neurite extension by quantitating the percentage of cells expressing neurites one cell body diameter or more, number of neurites per cell, and length of longest neurite.

Using this assay, adding the compounds identified by the method of the invention to NG108-15 cells on MAG adsorbed surfaces markedly enhances neurite outgrowth.

B. In vitro assay for ganglioside effects on MAG inhibition of neurite outgrowth by observing neurite extension from cerebellar neurons on MAG-expressing Chinese hamster ovary (CHO) cells [following the method of Mukhopadhyay, G., et al., Neuron, 13:757, 1994]

To mimic the natural cellular presentation of MAG, CHO cells, transfected with the cDNA encoding MAG, are used as the substratum on which the primary cerebellar isolates can extend neurites. MAG-expressing and control CHO cells are cultured for 24 hours in 8-well tissue culture slides to form confluent monolayers. These monolayers are pre-treated with micromolar concentrations of identified compounds, e.g. glycolipids identified by the method of the invention, including gangliosides, as micelles or in liposomes, millimolar concentrations of ganglioside oligosaccharides, or with corresponding concentrations of control glycolipids and oligosaccharides.

Primary neuronal isolates from seven day old rat cerebella are harvested then trypsinized and resuspended as single cell suspensions in medium containing 2% fetal bovine serum. Co-cultures are established by adding 300 cerebellar neurons to the variably treated CHO monolayers in medium containing 2% fetal bovine serum, cultured for 16 hours, then fixed with 4% paraformaldehyde. The fixed cells are scored microscopically for neurite extension by quantitating percentage of cells expressing neurites one cell body diameter or more, number of neurites per cell, and length of longest neurite.

Using this assay, adding the compounds identified by the method of the invention to cerebellar cells on MAG-transfected CHO cells markedly enhances neurite outgrowth.

Example 5

Synthesis of Gangliosides

The purpose of these tests was to determine methods for synthesizing a $\beta$-series ganglioside GQ1$\beta$ (IVNeu5 Ac$\alpha_2$, III Neu5Ac$\alpha_2$-Gg$_4$Cer) (Y. Hirabayashi, A. Hyogo, T. Nakao, K. Tsuchiya, Y. Suzuki, M. Matsumoto, K. Kon and S. Ando, *J. Biol. Chem.,* 265:8144, 1990; K. Hotta, S. Komba, H. Ishida, M. Kiso and A. Hasegawa, J. Carbohydr. Chem., 13:665, 1994; H. Prabhanjan, K. Aoyama, M. Kiso and A. Hasegawa, *Carbohydr. Res.,* 223:87, 1992.) Described in detail below is the first total synthesis of $\beta$-series ganglioside GQ1$\beta$.

For the synthesis of a $\beta$-series ganglioside GQ1$\beta$, a well designed trisaccharide derivative 3 was selected as a key glycosyl acceptor, suitable for the preparation of the pentasaccharide derivative 5 and its transformation to the acceptor 6 for construction of the core structure of $\beta$-series gangliosides. This approach was taken considering the application for the synthesis of other $\alpha$- and $\beta$-series gangliosides containing $\alpha$-glycosidically-linked sialic acid at OH-6 of galactosamine residues.

General Methods. Optical rotations were determined with a Union PM-201 polarimeter at 25° C. and IR spectra were recorded with a Jasco IRA-100 spectrophotometer. $^1$H NMR spectra were recorded at 270 MHz with a Jeol JNM-GX 270 and at 500 Mhz with Varian VXR-500S spectrometers. Preparative chromatography was performed on silica gel (Fuji Silysia Co., 300 mesh) with the solvent systems specified. Concentrations were conducted in vacuo.

Example 5A 2-(Trimethylsilyl)ethyl O-(2-Acetamido-4,6-O-benzylidene-2-deoxy-3-O-levulinyl-$\beta$-D-galactopyranosyl)-

(1→4)-O-(2,3,6-tri-O-benzyl-β-D-galactopyranosyl)-(1→4)-2,3,6-tri-O-benzyl-β-D-glucopyranoside (Compound 2).

To a solution of 2-(trimethylsilyl)ethyl O-(2-acetamido-4,6-O-benzylidene-2-deoxy-β-D-galactopyranosyl)-(1→4)-O-(2,3,6-tri-O-benzyl-β-D-galactopyranosyl)-(1→4)-(2,3,6-tri-O-benzyl-β-D-glucopyranoside (K. Hotta, S. Komba, H. Ishida, M. Kiso and A. Hasegawa, *J. Carbohydr. Chem.,* 13:665, 1994.) (1:540 mg 0.42 mmol) in pyridine (10 mL) was added levulinic anhydride (181 mg, 0.84 mmol). The mixture was stirred for 2 h at room temperature, and MeOH (2 mL) was then added. The solution was concentrated to a syrup which was extracted with $CH_2Cl_2$. The extract was successively washed with 2M HCl acid and $H_2O$ dried ($Na_2SO_4$) and concentrated.

Column chromatography (1:3 EtOAc-hexane) of the residue on silica gel (20 g) gave 2 (476 mg, 82%) as an amorphous mass: $[\alpha]_D+34.3°$ (c 2.1, $CHCl_3$) $^1H$ NMR ($CDCL_3$) δ1.00 (m, 2H, $Me_3SiCH_2CH_2$), 1.80 (s, 3H. AcN), 2.18 (s, 3H, $CH_3COCH_2CH_2$), 5.59 (s, 1H, PhCH), and 7.22–7.58 (m, 35H, 7Ph).

Anal. Calcd for $C_{79}H_{93}NO_{18}Si$ (1372.7): C, 69.12; H, 6.83; N, 1.02. Found: C, 68.84; H, 6.64; N, 1.00.

Example 5B 2-(Trimethylsilyl)ethyl O-(2-Acetamido-2-deoxy-3-O-levulinyl-β-D-galactopyranosyl)-(1→4)-O-(2,3,6-tri-O-benzyl-β-D-galactopyranosyl)-(1→4)-O-(2,3,6-tri-O-benzyl-β-D-glucopyranoside (Compound 3).

To a solution of Compound 2 (417 mg, 0.30 mmol) in MeOH (10 mL) was added p-toluenesulfonic acid monohydrate (20 mg). The mixture was stirred for 1 h at room temperature, then neutralized with Amberlite IRA-410 (OH$^-$) resin and concentrated. Column chromatography (20:1 $CH_2Cl_2$-MeOH) of the residue on silica gel (20 g) gave Compound 3 (390 mg. quantitative) as an amorphous mass: $[\alpha]_D+15.4°$ (c 3.1 $CHCL_3$); $^1H$ NMR($CDCl_3$) δ1.03 (m, 2H, $Me_3SiCH_2CH_2$), 1.60 (s, 3H, AcN), 2.14 (s, 3H, $CH_3COCH_2CH_2$), 5.57 (s, 1H, $J_{1,2}$=7.7 Hz, H-1c), and 7.22–7.42 (m, 30H, 6Ph).

Anal. Calcd for Compound $3_{72}H_{89}NO_{18}Si$ (1284.6): C, 67.32; H, 6.98; N, 1.09. Found: C, 67.17; H, 6.78; N, 0.95.

Example 5C 2-(Trimethylsilyl)ethyl O-[Methyl 5-Acetamido-8 -O-(5-acetamido-4,7,8,9-tetra-O-acetyl-3,5-dideoxy-D-glycero-α-D-galacto-2-nonulopy-ranosylono-1',9-lactone)-4,7-di-O-acetyl-3,5-dideoxy-D-glycero-α-D-galacto-2-nonulopyranosylonate]-(2→6)-O-(2-acetamido-2-deoxy-3-O-levulinyl-β-D-galactopyranosyl)-(1→4)-O-2,3,6-tri-O-benzyl-β-D-galactopyranosyl)-(1→4)-O-2,3,6-tri-O-benzyl-β-D-glucopyranoside (Compound 5).

To a solution of Compound 3(571 mg, 0.30 mmol) and methyl [phenyl 5-acetamido-8-O-(5-acetamido-4,7,8,9-tetra-O-acetyl-3,5-dideoxy-D-glycero-α-D-galacto-2-nonulopyra-nosylono-1',9-lactone)-4,7-di-O-acetyl- 3,5-dideoxy-2-thio-D-glycero-D-galacto-2-nonulopyranosid]onate (H. K. Ishida, Y. Ohta, Y. Tsukada, M. Kiso and A. Hasegawa, *Carbohydr. Res.,* 246:75, 1993) (4; 390 mg, 0.60 mmol) in MeCN (8 mL) were added 3Å molecular sieves (1.5 g). The mixture was stirred for 5 h at room temperature, then cooled to −30° C. To the stirred mixture were added N-iodosuccinimide (NIS) (273 mg, 1.2 mmol) and trifluoromethanesulfonic acid (TfOH) (13 μL, 0.12 mmol), and stirring was continued for 10 h at −30° C. The solids were removed by filtration and washed with $CH_2Cl_2$. The combined filtrate and washings were successively washed with M $Na_2CO_3$ and M $Na_2S_2O_3$, dried ($Na_2SO_4$) and concentrated. Column chromatography (10:1 toluene-MeOH) of the residue on silica gel (20 g) gave Compound 5 (310 mg, 48%) as an amorphous mass: $[\alpha]_D$–1.2° (c 0.9, $CHCl_3$); $^1H$ NMR ($CDCl_3$) δ1.02 (m, 2H $Me_3SiCH_2CH_2$), 1.87–2.24 (10s, 30H, 3AcN, 6AcO, and $CH_3COCH_2CH_2$), 2.41 (dd, 1H $J_{gem}$=13.7 Hz, $J_{3eq,4}$=5.4 Hz, H-3eeq), 2.64 (dd, 1H, $J_{gem}$=12.8 Hz, $J_{3eq,4}$=4.9 Hz, H-3deq) 3.82 (s, 3H, MeO), 5.05 (m, 1H, H-4d), 5.37 (m, 1H, H-4e), 5.41 (d, 1H, $J_{7,8}$=8.6 Hz, H-7d), 5.44 (m, 1H, H-8e), and 7.25–7.40 (m, 30H, 6Ph).

Anal. Calcd for $C_{97}H_{135}N_3O_{39}Si$ (1995.2): C, 58.39; H, 6.82; N, 2.11. Found: C, 58.25; H, 6.54; N, 2.03.

Example 5D 2-(Trimethylsilyl)ethyl O-[Methyl 5-Acetamido-8-O-(5-acetamido-4,7,8,9-tetra-O-acetyl-3,5-dideoxy-D-glycero-α-D-galacto-2-nonulopy-ranosylono-1', 9-lactone)-4,7-di-O-acetyl-3,5-dideoxy-D-glycero-α-D-galacto-2-nonulopyranosylonate]-(2→6)-O-(2-acetamido- 2-deoxy-β-D-galactopyranosyl)-(1→4)-O-(2,3,6-tri-O-benzyl-β-D-galactoopyranosyl)-(1→4)-O-(2,3,6-tri-O-benzyl-β-D-glucopyranoside (Compound 6). To a solution of Compound 5 (310 mg, 0.15 mmol) in EtOH (3 mL) was added hydrazine acetate (270 mg) (H. Nagaoka, W. Rutsch, G. Schmidt, H. Illo, M. R. Johnson and Y. Kishi, *J. Am. Chem, Soc.,* 102:7962, 1980). The mixture was stirred for 0.5 h at room temperature and then concentrated. Column chromatography (30:1 $CH_2Cl_2$MeOH) of the residue on silica gel (20 g) gave Compound 6 (170 mg, 57%) as an amorphous mass: $[\alpha]_D+8.9°$ (c 2.0 $CHCl_3$); $^1H$ NMR ($CDCl_3$) δ1.01 (m, 2H, $Me_3SiCH_2CH_2$), 1.87–2.25 (9s, 27H, 6AcO and 3AcN), 2.47 (m, 1H, H-3deq), 2.63 (dd, 1H, $J_{gem}$=12.7 Hz, $J_{3eq,4}$=5.1 Hz, H-3eeq), 3.79 (s, 3H, MeO), and 7.26–7.38 (m, 30H, 6Ph).

Anal. Calcd for $C_{92}H_{129}N_3O_{37}Si$ (1897.1): C, 58.25; H, 6.85; N, 2.21. Found: C, 58.08; H, 6.81; N, 2.14.

Example 5E 2-(Trimethylsilyl)ethyl O-[Methyl 5-Acetamido-8-O-(5-acetamido-4,7,8,9-tetra-O-acetyl-3,5-dideoxy-D-glycero-α-D-galacto-2-nonulopy-ranosylono-1'9-lactone)-4,7-di-O-acetyl-3,5-dideoxy-D-glycero-α-D-galacto-2-nonulopyranosylonate]-(2→3)-O-(2,4,6-tri-O-benzoyl-β-D-galactopyranosyl)-(1 →3)-{O-[methyl 5-Acetamido-8-O-(5-acetamido-4,7,8,9-tetra-O-acetyl-3,5-dideoxy-D-glycero-α-D-galacto-2-nonulopy-ranosylono-1',9-lactone)-4,7-di-O-acetyl-3,5-dideoxy-D-glycero-α-D-galacto-2-nonuloppyranosylonate]-(2→6)}-O-(2-acetamido-2-deoxy-β-D-galactopyranosyl)-(1→4)-O-(2,3,6-tri-O-benzyl-β-D-galactopyranosyl)-(1→4)-O- 2,3,6-tri-O-benzyl-β-D-glucopyranoside (Compound 8).

To a solution of Compound 6 (50 mg, 0.024 mmol) and methyl O-[methyl 5acetamido-8-O-(5--acetamido-4,7,8,9-tetra-O-acetyl-3,5-dideoxy-D-glycero-α-D-galacto-2-nonulopyranosylono-1'9-lactone)-4,7-di-O-acetyl-3,5-dideoxy-D-glycero-α-D-galacto-2-nonulopyranosylonate]-(2→3)-2,4,6-tri-O-benzoyl-1-thio-βD-galactopyranoside (H. K. Ishida, H. Ishida, M. Kiso and A. Hasegawa, *Carbohydr. Res.,* 260:cl, 1994) (7, 65 mg, 0.05 mmol) in $CH_2Cl_2$ (1 mL) were added 4 Å molecular sieves (100 mg). The mixture was stirred for 5 h at room temperature then cooled to 0° C. To the mixture was added, with stirring, dimethyl (methylthio)sulfonium triflate (a) P. Fugedi and P. J. Garegg, *Carboyhydr. Res.,* 149:c9, 1986); b) O. Kanie, M. Kiso and A. Hasegawa, *J. Carbohydr. Chem.,* 7:501, 1988) (DMTST; 25 mg, 0.1 mmol), and stirring was continued for 1 day at 0° C. The precipitates were removed by filtration, and washed thoroughly with $CH_2Cl_2$. The filtrate and washings were combined, and the solution was successively washed with M $Na_2CO_3$ and $H_2O$, dried ($Na_2SO_4$) and concentrated. Column chromatography (20:1 $CH_2Cl_2$—MeOH) of the residue on silica gel (50 g) gave Compound 8 (33 mg, 42%) as an amorphous mass: $[\alpha]_D+8.4°$ (c 0.6, $CHCl_3$); $^1H$ NMR ($CDCl_3$) δ1.00 (m, 2H, $Me_3SiCH_2CH_2$), 1.81–2.18 (17s, 51H, 5AcN and 12AcO), 2.39–2.64 (m, 4H, H-3eeq, H-3feq, H-3geq, and H-3heq), 3.50 and 3.82 (2s, 6H, 2MeO), and 7.18–8.20 (m, 45H, 9 Ph).

Anal. Calcd for $C_{164}H_{197}N_5O_{66}Si$ (3322.4): C, 59.29; H, 5.98; N, 2.11. Found: C, 58.99; H, 5.72; N, 1.84.

Example 5F 2-(Trimethylsilyl)ethyl O-[Methyl 5-Acetamido-8-O-(5-acetamido-4,7,8,9-tetra-O-acetyl-3,5-dideoxy-D-glycero-α-D-galacto-2-nonulopyranosylono-1',9-lactone)-4,7-di-O-acetyl-3,5-dideoxy-D-glycero-α-D-galacto-2-nonulopyranosylonate]-(2→3)-O-(2,4,6-tri-O-benzoyl-β-D-galactopyranosyl)-(1→3)-{O-[methyl 5-Acetamido-8-O-[5-acetamido-4,7,8,9-tetra-O-acetyl-3,5-dideoxy-D-glycero-α-D-galacto-2-nonulopyranosylono-1',9-lactone)-4,7-di-O-acetyl-3,5-dideoxy-D-glycero-α-D-galacto-2-nonulopyransylonate](2→6)}-O-(2-acetamido-4-O-acetyl-2-deoxy-β-D-galactopyranosyl)-(1→4)-O-(2,3,6-tri-O-acetyl-β-D-galactopyranosyl)-(1→4)-O-2,3,6-tri-O-acetyl-β-D-glucopyranoside (Compound 9)

A solution of Compound 8 (290 mg, 87 μmol) in EtOH (20 mL) and AcOH (4 mL) was hydrogenated in the presence of 10% Pd—C (500 mg) for 2 days at 40° C., the catalyst removed by filtration and the solution concentrated. The residue was acetylated with $Ac_2O$ (5 mL) and pyridine (10 mL) for 16 h at room temperature. The product was purified by chromatography (20:1 $CH_2Cl_2$—MeOH) on a column of silica gel (20 g) to give Compound 9 (180 mg, 67%) as an amorphous mass: $[\alpha]_D-17.1°$ (c 1.8, $CHCl_3$)$^1H$ NMR ($CDCl_3$) δ0.89 (m, 2H, $Me_3SiCH_2CH_2$), 1.89–2.19 (m, 72H, 19AcO and 5AcN), 2.32–2.51 (m, 4H, H-3ceq, H-3feq, H-3geq, and H3heq), 3.24 and 3.72 (2s, 6H, 2MeO), 5.77 (d, 1H, $J_{3,4}$=3.8 Hz, H-4c), and 7.36–8.19 (m, 15H, 3Ph).

Anal. Calcd for $C_{136}H_{175}N_5O_{73}Si$ (3075.94): C, 53.11; H, 5.73; N, 2.28. Found: C, 53.03; H, 5.60; N, 1.99.

Example 5G

O-[Methyl 5-Acetamido-8-O-(5-acetamido-4,7,8,9-tetra-O-acetyl-3,5-dideoxy-D-glycero-α-D-galacto-2-nonulopyranosylono-1',9-lactone)-4,7-di-O-acetyl-3,5-dideoxy-D-glycero-α-D-galacto-2-nonulopyranosylonate]-(2→3)-O-(2,4,6-tri-O-benzoyl-β-D-galactopyranosyl)-(1→3)-{O-[methyl 5-Acetamido-8-O-(5-acetagmido-4,7,8,9-tetra-O-acetyl-3,5-dideoxy-D-glycero-α-D-galacto-2-nonulopyranolylono-1',9-lactone)-4,7-di-O-acetyl-3,5-dideoxy-D-glycero-α-D-galacto-2-nonulopyranosylonate]-(2→6)}-O-(2-acetamido-4-O-acetyl-2-deoxy-β-D-galactopyranosyl)-(1→4)-O-2,3,6-tri-O-acetyl-β-D-galactopyransoyl)-(1→4)-O-2,3,6-tri-O-acetyl-D-glucopyranose (Compound 10).

To a solution of Compound 9 (180 mg, 59 μmol) in $CH_2Cl_2$ (3 mL) was added $CF_3CO_2H$ (K. Jansson, S. Ahlfors, T. Frejd, J. Kihlberg, g. Magmusson, J. Dahmen, G. Noori and K. Stenvall, *J. Org. Chem.,* 53:5629, 1988); (0.5 mL) at 0° C., and the mixture was stirred for 0.5 h at 0° C., and concentrated. Column chromatography (20:1 $CH_2Cl_2$MeOH) of the residue on silica gel (10 g) gave 10 (150 mg, 86%) as an amorphous mass: IR (KBr) 3600–3300 (OH, NH), 1740 and 1230 (ester), 1670 and 1550 (amide), and 760 and 720 $cm^{-1}$(Ph).

Anal. Calcd for $C_{131}H_{163}N_5O_{73}$ (2975.71): C. 52.88; H, 5.52; N. 2.35. Found C. 52.72; H, 5.35; N, 2.17.

Example 5H

O-[Methyl 5-Acetamido-8-O-(5-acetamido-4,7,8,9-tetra-O-acetyl-3,5-dideoxy-D-glycero-α-D-galacto-2-nonulopyranolylono-1',9-lactone)-4,7-di-O-acetyl- 3,5-dideoxy-D-glycero-α-D-galacto-2-nonulopyranosylonate]-2→3)-O-(2,4,6-tri-O-benzoyl-β-D-galactopyranosyl)-(1→3)-{O-[methyl 5-Acetamido-8-O-(5-acetamido-4,7,8,9-tetra-O-acetyl-3,5-dideoxy-D-glycero-α-D-galacto-2-nonulopyranosylono-1',9-lactone)-4,7-di-O-acetyl-3,5-dideoxy-D-glycero-α-D-galacto-2-nonulopyranosylonate]-(2→6)}-O-(2-acetamido-4-O-acetyl-2-deoxy-β-D-galactopyranosyl)-(1→4)-O-(2,3,6-tri-O-acetyl-β-D-galactopyranosyl)-(1→4)-O-2,3,6-tri-O-acetyl-α-D-glucopyranosyl Trichloroacetimidate (Compound 11)

To a solution of Compound 10 (150 mg, 50 μmol) in $CH_2Cl_2$ (2 mL) and trichloroacetonitrile (0.4 mL) at −5° C. was added 1,8-diazabicyclo[5.4.0]undec-7-enc(DBU, 10 mg), and the mixture was stirred for 1 h at 0° C., then concentrated. Column chromatography (20:1 $CH_2Cl_2$-MeOH) of the residue on silica gel (10 g) gave 11 (145 mg, 92%) as an amorphous mass: $[\alpha]_D-3.44°$ (c2.9$CHCl_3$)$^1H$ NMR ($CDCl_3$) δ1.87–2.19 (m, 72H, 19AcO and 5AcN), 2.36–2.46 (m, 4H, H-3eeq, H-3feq, H-3geq, and H-3heq), 3.24 and 3.70 (2s, 6H, 2MeO), 6.49 (d, 1H, $J_{1,2}$=3.7 Hz,H-1a), 7.31–8.19 (m, 15H, 3Ph), 8.69 (s, 1H, C≡NH).

Anal. Calcd for $C_{133}H_{163}N_6O_{73}Cl_3$ (3120.1): C, 51.20; H, 5.27: N, 2.69. Found: C, 51.03; H, 4.99; N, 2.56.

Example 5I

O-[Methyl 5-Acetamido-8-O-(5-acetamido-4,7,8,9-tetra-O-acetyl-3,5-dideoxy-D-glycero-α-D-galacto-2-nonulopyranolylono-1',9-lactone)-4,7-di-O-acetyl-3,5-dideoxy-D-glycero-α-D-galacto-2-nonulopyranosylonate]-(2→3)-O-(2,4,6-tri-O-benzoyl-β-D-galactopyranosyl)-(1→3)-{O-[methyl 5-Acetamido-8-O-(5-acetamido-4,7,8,9-tetra-O-acetyl-3,5-dideoxy-D-glycero-α-D-galacto-2-nonulopyranosylono-1',9-lactone)-4,7-di-O-acetyl-3,5-dideoxy-D-glycero-α-D-galacto-2-nonulopyransylonate](2→6)}-O-(2-acetamido-4-O-acetyl-2-deoxy-β-D-galactopyranosyl)-(1→4)-O-(2,3,6-tri-O-acetyl-β-D-galactopyranosyl)-(1→4)-(2,3,6-tri-O-acetyl-β-D-glucopyranosyl)-(1→1)-(2S,3R,4E)-2-azido-3-O-benzoly 4-octadecene-1,3-diol (Compound 13)

To a solution of Compound 11 (145 mg, 46μmol) and (2S, 3R, 4E)-2-azido-3-O-benzoyl-4octadecene-1,3-diol (a) Y. Ito M. Kiso and A. Hasegawa, *J. Carbohydr. Chem.,* 8:285, 1989; b) R. R. Schmidt and P. Zimmermann, *Angew. Chem. Intl. Ed. Engl.,* 25:725, 1986); R. R. Schmidt and G. Grundler, *Synthesis,* 885:(1981).) (12, 55 mg, 110 μmol) in $CH_2Cl_2$ (2 mL) was added 4 Å molecular sieves (AW-300, 0.5 g). The mixture was stirred for 5 h at room temperature, then cooled to 0° C. Trimethylsilyl trifluoromethanesulfonate (30 μL) was added, and the mixture was stirred for 3 h at 0° C. and then filtered. The insoluble materials were washed with $CH_2Cl_2$, and the combined filtrate and washings were washed with M $NaHCO_3$ and $H_2O$, dried ($Na_2SO_4$) and concentrated. Column chromatography (20:1 $CH_2Cl_2$-MeOH) of the residue on silica gel (10 g) gave Compound 13 (93 mg, 59%) as an amorphous mass: $[α]_D$-14.3° (c 1.9 $CHCl_3$); $^1H$ NMR ($CDCl_3$) δ0.88 (t,3H, $J_{Me,CH2}$=6.2 Hz, $MeCH_2$), 1.24 (s, 22H, 11 $CH_2$), 1.84–2.17 (m, 72H, 19AcO and 5AcN), 2.32–2.46 (m, 4H, H-3eeg, H-3feq, H-3geq, and H-3heq), 3.25 and 3.69 (2s, 6H, 3MeO), 5.90 (m, 1H,H-5 of sphingosine), 7.28–8.28(m, 20H, 4Ph).

Anal. Calcd for $C_{156}H_{200}N_8O_{75}$ (3387.3): C, 55.32 H, 5.95; N, 3.31, Found: C, 55.29; H, 5.77; N, 3.29.

Example 5J

O-[Methyl 5-Acetamido-8-O-(5-acetamido-4,7,8,9-tetra-O-acetyl-3,5-dideoxy-D-glycero-α-D-galacto-2-nonulopyranolylono-1',9-lactone)-4,7-di-O-acetyl-3,5-dideoxy-D-glycero-α-D-galacto-2-nonulopyranosylonate]-(2→3)-O-(2,4,6-tri-O-benzoyl-β-D-galactopyranosyl)-(1→3)-{O-[methyl 5-Acetamido-8-O-(5-acetamido-4,7,8,9-tetra-O-acetyl-3,5-dideoxy-D-glycero-α-D-galacto-2-nonulopyranosylono-1',9-lactone)-4,7-di-O-acetyl-3,5-dideoxy-D-glycero-α-D-galacto-2-nonulopyranosylonate]-(2→6}-O-(2-acetamido-4-O-acetyl-2-deoxy-β-D-galactopyranosyl)-(1→4)-(2,3,6-tri-O-acetyl-β-D-glucopyranosyl)-(1→4)-(2,3,6-tri-O-acetyl-βD-glucopyranosyl)-(1→1)-(2S, 3R, 4E)-3-O-benzoyl-2-octadecanamido-4-octadecene-1,3-diol (Compound 14)

Hydrogen sulfide was bubbled (Y. Ito M. Kiso and A. Hasegawa, *J. Carbohydr. Chem.*, 8:285,1989; T. Adachi, Y. Yamada, I. Inoue and M. Saneyosi, *Synthesis*, 45, 1977) through a stirred solution of Compound 13 (93 mg, 27 μmol) in aqueous 83% pyridine (13 mL) for 3 days at 0° C. The mixture was concentrated, and the residue was stirred with octadecanoic acid (25 mg, 95 μmol) and 1-ethyl-3-(3-dimethylaminopropyl)carbodimide hydrochloride (25 mg, 138 μmol) in $CH_2Cl_2$ (5 mL) for 1 day at room temperature. Dichloromethane (20 mL) was added, and the mixture was washed with $H_2O$, dried ($Na_2SO_4$) and concentrated. Column chromatography (20:1 $CH_2Cl_2$—MeOH) of the residue on silica gel (10 g) gave Compound 14 (85 mg, 85%) as an amorphous mass: $[α]_D$-12.9° (c1.7 $CHCl_3$); $^1H$ NMR ($CDCl_3$) δ0.88 (t, 6H, $J_{ME,CH2}$=7.0 Hz, $2MeCH_2$), 1.26 (s, 52H, $26CH_2$), 1.88–2.18 (24s, 72H, 19AcO and 5AcN), 2.32–2.46 (m, 4H, H-3eeq, H-3feq, H-3geq, and H-3heq), 3.26 and 3.77 (2s, 6H, 2MeO), 5.84 (m, 1H, H-5 of sphingosine), 7.34–8.21 (m, 20H, 4Ph).

Anal. Calcd for $C_{174}H_{236}N_6O_{76}$ (3627.8): C, 57.61; H, 6.56; N, 2.32, Found: C, 57.40; H, 6.51; N, 2.15.

Example 5K

Ganglioside GQ1β (Compound 15)

To a solution of Compound 14 (85 mg, 23 μmol) in MeOH (5 mL) was added a catalytic amount of NaOMe, and the mixture was stirred for 72 h at room temperature. Water (0.5 mL) was added, and the mixture was stirred for 10 h at room temperature, then neutralized with Amberlite IR-120($H^+$) resin. The resin was filtered off and washed with 1:1 $CHCl_3$—MeOH, and the combined filtrate and washings were concentrated. Column chromatography (1:1 $CHCl_3$-MeOH) of the residue on Sephadex LH-20 (10 g) gave Compound 15 (49 mg, 86%) as an amorphous solid; $[α]_D$+24.9° (c 1.0,1:1 $CHCl_3$—MeOH); $^1H$ NMR(1:1 DMSO-$d_6$-$D_2O$) δ0.86 (t,6H, $J_{Me,CH2}$=7.0 Hz, $2MeCH_2$), 1.23 (s, 52H, $26CH_2$), 1.85–1.89(5s, 15H, 5AcN), 2.42–2.73 (m, 4H, H-3eeq, H-3feq, H-3geq, and H-3heq), 4.22 (d, 1H, $J_{1,2}$=7.5 Hz, H-1a), 4.32(m, 2H, H-1b and H-1d), 4.70 (d, 1H, $J_{1,2}$=8.6 Hz, H-1c), 5.35 (m, 1H,H-4 of sphingosine), and 5.55 (m, 1H,H-5 of sphingosine).

Anal. Calcd for $C_{106}H_{182}N_6O_{55}$(2420.6): C, 52.60; H, 7.58; N, 3.47, Found: C, 52.34; H, 7.30; N, 3.23.

RESULTS

The appropriately protected trisaccharide acceptor Compound 3 was obtained in good yield from 2-(trimethylsilyl) ethyl O-(2-acetamido-4,6-O-benzylidene-2-deoxy-β-D-galactopyranosyl)-(1→4)-O-2,3,6-tri-O-benzyl-β-D-glucopyranoside (K. Hotta, S. Komba, H. Ishida, M. Kiso and A. Hasegawa, *J. Carbohydr. Chem.*, 13:665, 1994) (Compound 1) by 3-O-levulinylation and removal of the benzylidene group. The glycosylation of the trisaccharide acceptor Compound 3 with methyl [phenyl 5-acetamido-8-O-(5-acetamido-4,7,8,9-tetra-O-acetyl-3,5-dideoxy-D-glycero-D-galacto-2-nonulopyranosylono-1',9-lactone)-4,7-di-O-acetyl-3,5-dideoxy-2-,thio-D-glycero-D-galacto-2-nonulopyranosid]obate (Compound 4) by use of N-iodosuccinimide (NIS)—trifluoromethanesulfonic acid (TfOH) in the presence of powdered molecular sieves 3 Å (Ms-CÅ) in acetonitrile for 10 h at −30° C. gave the expected pentasaccharide α-glycoside Compound 5 in 48% yield. The observed chemical shifts and coupling constants of the sialyl α(2→8) sialic acid residue were a one-proton doublet of doublets at δ62.41 ($J_{gem}$=13.7 Hz, $J_{3eq,4}$=5.4 Hz, H-3eeq), a one-proton doublet of doublets at δ2.64 ($J_{gem}$=12.8 Hz, $J_{3eq,4}$=4.9 Hz, H-3 deq), a three-proton singlet at δ3.82 (MeO), a one-proton multiplet at δ5.05 (H-4d), a one-proton multiplet at δ5.37 (H-4e), a one-proton doublet at δ5.41 ($J_{7,8}$=8.6 Hz, H-7d), and a one-proton multiplet at δ5.44 (H-8e), which indicated that the newly formed glycosidic linkage was α (H. K. Ishida, Y. Ohta, Y. Tsukada, M. Kiso and A. Hasegawa, *Carbohydr. Res.*, 246:75, 1993.) The regiochemistry was deduced from the $^1H$ NMR spectrum of the acetylated Compound 5, the observed chemical shift of the N-acetylgalactosamine residue for H-4 (δ5.17), which indicated that the glycosylated position in Compound 5 was HO-6 of the GalNAc residue.

By removal (H. Nagaoka, W. Rutsch, G. Schmidt, H. Illo, M. R. Johnson and Y. Kishi, *J. Am. Chem, Soc.*, 102:7962, 1980) of the levulinyl group, the pentasaccharide acceptor Compound 6 was formed from Compound 5 in 57% yield. Dimethyl(methylthio)-sulfonium triflate (a) P. Fugedi and P. J. Garegg, *Carboyhydr. Res.*, 149:c9, 1986; b) O. Kanie M. Kiso and A. Hasegawa, *J. Carbohydr. Chem.*, 7:501, 1988) (DMTST)-promoted glycosylation of Compound 6 with methyl O-[methyl 5-acetamido-8-O-(5-acetamido-4,7,8,9-tetra-O-acetyl-3,5-dideoxy-D-glycero-α-D-galacto-2-nonulopyranolylono-1',9- lactone)-4,7-di-O-acetyl-3,5-dideoxy-D-glycero-α-D-galacto-2-nonulopyranosylonate]-(→3)-2,4,6-tri-O-benzoyl-1-thio-β-D-galactopyranoside (H. K. Ishida, H. Ishida, M. Kiso A. Hasegawa, *Carbohydr. Res.*, 260:cl, 1994) (Compound 7) in dichloromethane for 2 days at 0° C. gave the desired octasaccharide, Compound 8, in 42% yield. The regiochemistry of Compound 8 was deduced from the $^1$H NMR spectrum of the acetylated Compound 9. The observed chemical shift of GalNAc unit for H-4(δ5.77) indicated the position of glycosylation in Compound 8 to be HO-3. Catalytic hydrogenolysis (10% Pd—C) of the benzyl groups of Compound 8 in ethanol-acetic acid for 2 days at 40° C. and subsequent O-acetylation gave the per-O-acyl derivative 9 in 67% yield. Treatment of Compound 9 with trifluoroacetic acid in dichloromethane for 1 h at 0° C. gave the 1-hydroxy Compound 10. When treated with trichloroacetonitrile in dichloromethane in the presence of 1,8-diazabicyclo[5.4.0] undec-7-ene(DBU) for 1 h at 0° C. Compound 10 gave the α-trichloroacetimidate Compound 11 in 92% yield. The $^1$H NMR data for the Glc unit in Compound 11 [δ6.49 (J$_{1,2}$=3.7 Hz, H-1a), 8.69 (C=NH)] indicated the imidate to be α.

The final glycosylation of (2S,3R,4E)-2-azido-3-O-benzoyl-4-octadecene-1,3-diol (Compound 12) with Compound 11 in dichloromethane in the presence of boron trifluoride etherate for 3 h at 0° C. afforded the desired β-glycoside Compound 13 in 59% yield. Selective reduction of azido group in Compound 13 with hydrogen sulfide in aqueous 83% pyridine for 3 days at 0° C. gave the amine which on condensation with octadecanoic acid using 1-ethyl-3-(3-dimethylaminopropyl) carbodimide (WSC) in dichloromethane, gave the acylated GQ1β ganglioside Compound 14 in 36% yield after chromatography.

Finally, O-deacylation of Compound 14 with sodium methoxide in methanol, and subsequent saponification of the methyl ester group yielded the desired β-series ganglioside GQ1β, Compound 15, in 86% yield after chromatography on a column of Sephadex LH-20. The $^1$H NMR data of the product thus obtained was consistent with the structure assigned.

Ganglioside GT1β (Compound 23)

The invention achieves the synthesis of GT1β 23 as follows:

To a solution of 6 (50 mg, 0.024 mmol) and methyl O-(methyl 5-acetamido-4,7,8,9-tetra-O-acetyl-3,5-dideoxy-D-glycero-α-D-galacto-2-nonulopyranosylonate)-(2→3)-2,4,6-tri-O-benzoyl-1-thio-β-D-galactopyranoside (Kameyama, A., et al. Carbohydrate Research 200:269–285, (16, 0.05 mmol) in CH$_2$Cl$_2$ (1 mL) are added 4 Å molecular sieves (100 mg). The mixture is stirred for 5 h at room temperature then cooled to 0° C. To the mixture is added, with stirring, dimethyl(methylthio)sulfonium triflate (P. Fugedi and P. J. Garegg, *Carboyhydr. Res.*, 149:c9, 1986; O. Kanie, M. Kiso and A. Hasegawa, *J. Carbohydr. Chem.*, 7:501, 1988)(DMTST; 25 mg, 0.1 mmol), and stirring is continued for 1 day at 0° C. The precipitates are removed by filtration, and washed thoroughly with CH$_2$Cl$_2$. The filtrate and washings are combined, and the solution is successively washed with M Na$_2$CO$_3$ and H$_2$O, dried (Na$_2$SO$_4$), concentrated and purified to yield compound 17.

Starting with compound 17 and using the same steps as taken in Examples 5F–5K above, GT1β, Compound 23, is synthesized as follows: Compound 17 is converted into αtrichloroacetimidate, Compound 20, via reductive removal of the benzyl groups, O-acetylation, removal of the 2-(trimethylsilyl)ethyl group, and treatment with trichloroacetonitrile, which, on coupling with (2S,3R,4E)-2-azido-3-O-benzoyl-4-octadecene-1,3-diol (Compound 12), gives the β-glycoside, Compound 21. Finally, Compound 21 is transformed, via selective reduction of the azido group, coupling with octadecanoic acid, O-deacylation, and hydrolysis of the methyl ester group, into Compound 23, the GT1β ganglioside, in good yield.

The invention having been fully described, modifications within its scope will be apparent to those of ordinary skill in the art. All such modifications are deemed to be within the scope of the invention and the appended claims.

What is claimed is:

1. A method for stimulating neuronal cell growth, comprising contacting nerve cells with a composition comprising a therapeutically effective amount of a complex carbohydrate having the terminal sequence:

NeuAc-Gal-A-B-C-L wherein

A is substituted with two sialic acid groups, the linkage between the two sialic acid groups being NeuAc α2,8 NeuAc;

B is galactose;

C is glucose;

L is H or a hydrophobic group; and wherein the linkage of NeuAc-Gal is NeuAc α2,3 Gal thereby stimulating neuronal cell growth.

2. The method of claim 1, wherein L is an aglycon.

3. The method of claim 2 wherein the aglycon is selected from the group consisting of ethanols, octanols, phenols, alkyl alcohols, aryl alcohols, and ceramides.

4. The method of claim 1 wherein L is ceramide.

5. The method of claim 1, wherein A is substituted with one to three sialic acid groups.

6. The method of claim 5 wherein the linkage between the sialic acid group and A is NeuAc α2,6 GalNAc.

7. The method of claim 5 wherein B is substituted with one to three sialic acid groups.

8. The method of claim 7 wherein the linkage between B and the substituted one to three sialic acid groups is NeuAc α2,3 Gal.

9. The method of claim 7 wherein B is substituted with two sialic acid groups, the linkage between the two sialic acid groups being NeuAc α2,8 NeuAc.

10. The method of claim 1 wherein A and B are substituted with one to three sialic acid groups.

11. The method of claim 1 wherein Gal-A-B-C is a gangliotetraose.

12. The method of claim 1 wherein the composition comprises a pharmaceutically acceptable carrier.

13. The method of claim 1 wherein the complex carbohydrate is selected from the group consisting of GQ1bα, GT1b, GD1a, GT1β, and GM1b.

14. A complex carbohydrate having the structure:

NeuAc NeuAc NeuAc-Gal-A-B-C-L wherein the linkage of NeuAc-Gal is NeuAc α2,3 Gal, and wherein Gal-A-B-C is gangliotetraose, and L is H or a hydrophobic group, and wherein the complex carbohydrate binds to myelin-associated glycoprotein and induces axonal growth when a therapeutically effective amount of the complex carbohydrate is brought in contact with injured nerve cells.

15. The complex carbohydrate of claim 14 wherein L is an aglycon.

16. The complex carbohydrate of claim 15 wherein the aglycon is selected from the group consisting of ethanols, octanols, phenols, alkyl alcohols, aryl alcohols, and ceramides.

17. The complex carbohydrate of claim 14 wherein L is ceramide.

18. The complex carbohydrate of claim 14 wherein the linkage between the disialic group and Gal is NeuAc α2,6 Gal and the linkage between the two sialic acid of the disaialic acid is NeuAc α2,8 NeuAc.

19. The complex carbohydrate of claim 14 having the structure NeuAc α2,3 Gal β1,3(NeuAc α2,8 NeuAc α2,6) GalNAc β1,4 Gal β1,4 Glc β1,1'Cermide.

20. The complex carbohydrate of claim 14 further comprising a pharmaceutically acceptable carrier.

* * * * *